US010308703B2

(12) United States Patent
Aharoni et al.

(10) Patent No.: US 10,308,703 B2
(45) Date of Patent: Jun. 4, 2019

(54) VARIANTS OF DR3 AND USE THEREOF

(71) Applicant: THE NATIONAL INSTITUTE FOR BIOTECHNOLOGY IN THE NEGEV LTD., Beer-Sheva (IL)

(72) Inventors: Amir Aharoni, Beit Kama (IL); Itay Levin, Tel Aviv (IL)

(73) Assignee: THE NATIONAL INSTITUTE FOR BIOTECHNOLOGY I, Beer-Sheva (IL)

( * ) Notice: Subject to any disclaimer, the term of this patent is extended or adjusted under 35 U.S.C. 154(b) by 0 days.

(21) Appl. No.: 15/306,822

(22) PCT Filed: Apr. 27, 2015

(86) PCT No.: PCT/IL2015/050435
§ 371 (c)(1),
(2) Date: Oct. 26, 2016

(87) PCT Pub. No.: WO2015/166486
PCT Pub. Date: Nov. 5, 2015

(65) Prior Publication Data

US 2017/0114118 A1 Apr. 27, 2017

Related U.S. Application Data

(60) Provisional application No. 61/984,910, filed on Apr. 28, 2014.

(51) Int. Cl.
*C07K 14/715* (2006.01)
*C12N 5/10* (2006.01)
(Continued)

(52) U.S. Cl.
CPC ...... *C07K 14/70578* (2013.01); *C07K 14/715* (2013.01); *A61K 38/00* (2013.01); *C07K 2319/30* (2013.01)

(58) Field of Classification Search
None
See application file for complete search history.

(56) References Cited

U.S. PATENT DOCUMENTS

| | | | | |
|---|---|---|---|---|
| 8,846,874 B2 * | 9/2014 | Jung | C07K 19/00 424/178.1 |
| 9,649,347 B2 * | 5/2017 | Chen | A61K 35/747 |
| 2012/0263718 A1 | 10/2012 | Siegel | |

FOREIGN PATENT DOCUMENTS

| | | | |
|---|---|---|---|
| WO | 2005018571 A2 | 3/2005 |
| WO | 2006127900 A2 | 11/2006 |
| WO | 2012117067 A1 | 9/2012 |

OTHER PUBLICATIONS

Strausberg et al., Tumor necrosis factor receptor superfamily, member 25 [Mus musculus], GenBank Database, Accession No. AAH17526, version AAH17526.1 [Retrieved online Dec. 11, 2017]. Sep. 14, 2006.*

(Continued)

*Primary Examiner* — Claire Kaufman
(74) *Attorney, Agent, or Firm* — The Roy Gross Law Firm, LLC; Roy Gross

(57) ABSTRACT

Death-domain receptor 3 (DR3) variants having increased binding affinity to TL1A, and composition comprising same, are provided. Further, methods of use of said peptides or composition, including, but not limited to treatment of autoimmune and/or inflammatory disease are provided.

10 Claims, 11 Drawing Sheets

Specification includes a Sequence Listing.

(51) Int. Cl.
*C12N 15/11* (2006.01)
*C07K 14/705* (2006.01)
*A61K 38/00* (2006.01)

(56) References Cited

OTHER PUBLICATIONS

UniiProt Accession No. G2RU12, TNF receptor superfamily member 25 [Gorilla gorilla gorilla]. [Retrieved on May 31, 2018], Retirieved from Internet: <URL: http://www.uniprot.org/uniprot/G3RU12>, Nov. 16, 2011.*
Chen et al., Fusion protein linkers: Property, design and functionality, Adv. Drug Deliv. Rev. 65(10):1357-1369, 2013.*
UniiProt Accession No. F7GXU5, TNF receptor superfamily member 25 [Macaca mulatta]. [Retrieved on May 31, 2018], Retirieved from Internet: <URL: http://www.uniprot.org/uniprot/F7GXU5>, Nov. 16, 2011.*
Meylan, Francoise, et al. "The TNF-family cytokine TL1A drives IL-13-dependent small intestinal inflammation." Mucosal immunology 4.2 (2011): 172-185. doi:10.1038/mi.2010.67; published online Oct. 27, 2010 Retrieved from the internet: http://www.nature.com/mi/journal/v4/n2/full/mi201067a.html; Oct. 27, 2011 (Oct. 27, 2011); p. 183 right column third paragraph,:figure 8.
Search Report and Written Opinion of PCT/IL2015/050435 Completed Aug. 12, 2015; dated Aug. 12, 2015 15 Pages.
Anonymous, "Predicted: tumor necrosis factor receptor superfamily member 25 [Ceratotherium simum simum]", Apr. 11, 2013, XP055408357.
Database Geneseq [Online], "Human death receptor 3 (DR3) mutant I43N/L45V", Oct. 25, 2012, XP002774058.

* cited by examiner

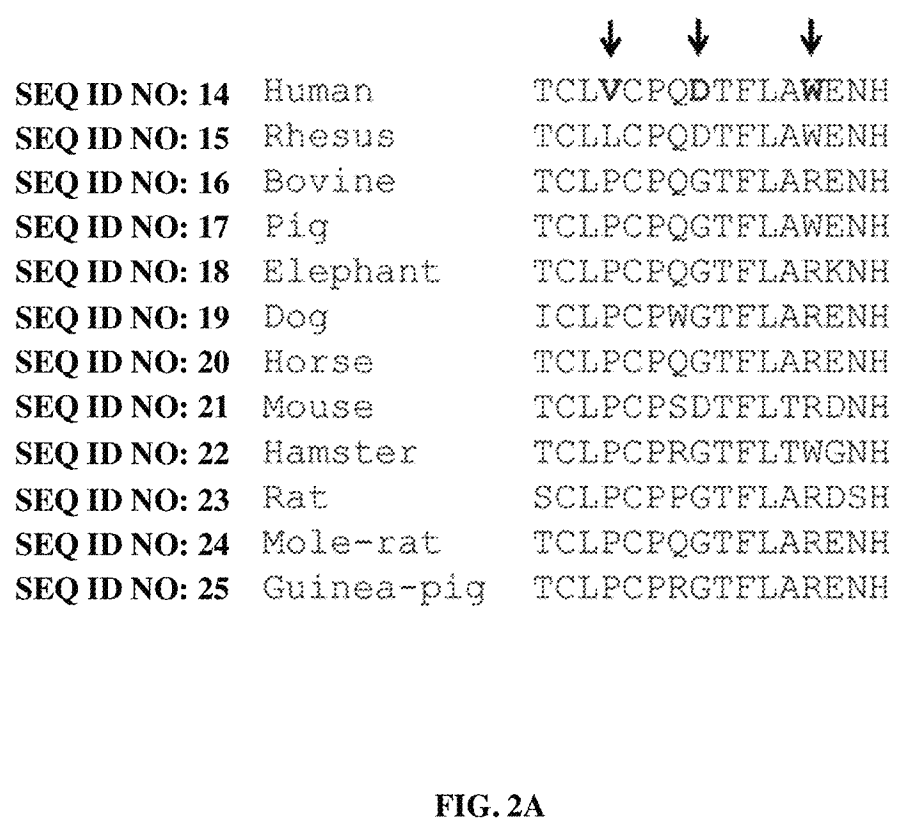

| | | |
|---|---|---|
| **SEQ ID NO: 14** | Human | TCL**V**CPQ**D**TFLA**W**ENH |
| **SEQ ID NO: 15** | Rhesus | TCLLCPQDTFLAWENH |
| **SEQ ID NO: 16** | Bovine | TCLPCPQGTFLARENH |
| **SEQ ID NO: 17** | Pig | TCLPCPQGTFLAWENH |
| **SEQ ID NO: 18** | Elephant | TCLPCPQGTFLARKNH |
| **SEQ ID NO: 19** | Dog | ICLPCPWGTFLARENH |
| **SEQ ID NO: 20** | Horse | TCLPCPQGTFLARENH |
| **SEQ ID NO: 21** | Mouse | TCLPCPSDTFLTRDNH |
| **SEQ ID NO: 22** | Hamster | TCLPCPRGTFLTWGNH |
| **SEQ ID NO: 23** | Rat | SCLPCPPGTFLARDSH |
| **SEQ ID NO: 24** | Mole-rat | TCLPCPQGTFLARENH |
| **SEQ ID NO: 25** | Guinea-pig | TCLPCPRGTFLARENH |

FIG. 2A

VARIANTS OF DR3 AND USE THEREOF

RELATED APPLICATIONS

This application is a National Phase of PCT Patent Application No. PCT/IL2015/050435 having International filing date of Apr. 27, 2015, which claims the benefit of priority of U.S. Patent Application No. 61/984,910 filed on Apr. 28, 2014. The contents of the above applications are all incorporated by reference as if fully set forth herein in their entirety.

FIELD OF INVENTION

This invention is directed to; inter alia, peptides derived from death-domain receptor 3 (DR3) effective in reducing interferon (IFN)-γ secretion, and methods of use thereof, including, but not limited to treatment of autoimmune and/or inflammatory disease.

BACKGROUND OF THE INVENTION

The mammalian immune system is a complex network of cells regulated by signals transmitted by many secreted and receptor proteins. The human tumor necrosis factor (TNF) superfamily includes at least 19 members and represents a major class of the stimulatory proteins. TNF-like 1A (TL1A), is a newly described member of the TNF superfamily that was shown to be involved in a range of autoimmune inflammatory diseases including inflammatory bowel diseases (IBD), Rheumatic Arthritis (RA), and Asthma. TL1A is currently the only known ligand for death-domain receptor 3 (DR3), which is predominantly expressed by activated T-cells and endothelial cells. Binding of TL1A to DR3 triggers proliferative signals probably through activation of NF-κB-associated pathways. It was shown that TL1A increases interferon (IFN)-γ production by acting in synergy with interleukin (IL)-12 and IL-18 and can thus bias the immune response towards a type 1 T helper cell (TH1) like response. It was first shown that TL1A is expressed by endothelial cells and its expression in these cells is significantly enhanced by treatments with TNF-α or IL-16. Subsequent studies have shown that TL1A is also expressed in lymphocytes plasma cells and monocytes especially in intestinal tissues from patients with inflammatory bowel diseases (IBD).

DR3, the receptor for TL1A, is expressed by CD4+ T cells and natural killer cells and its expression is increased upon T-cell activation. Although DR3 possesses an intracellular death domain that can lead to apoptosis, functional data suggest that the activity of DR3 is mainly pro-inflammatory. Interestingly, another natural receptor for TL1A is the Decoy Receptor 3 (DcR3), encoding a soluble protein that can bind TL1A with high affinity. This soluble receptor exhibit broad specificity and can bind other TNF ligands including FasL and LIGHT. Thus, it is difficult to define the contribution of DcR3 to host immunity due to the diverse functions of the three TNF ligands.

Using two distinct animal models for Chron's disease (CD) it was shown that the induction of intestinal inflammation is associated with significant up-regulation of TL1A and DR3 in the inflamed mucosa. Subsequent study using DR3 deficient mice show that DR3 expression is required on T cells for immunopathology including local T cell accumulation and cytokine production in Experimental Autoimmune Encephalomyelitis (EAE) and allergic lung inflammation disease models. Immunopathology and clinical disease were dramatically reduced in DR3 deficient mice both in mice model of lung inflammation and in EAE. In addition, it was shown that genetic variations in the TL1A gene contribute to the susceptibility to IBD in Japanese and European populations. Finally, several studies using experimental models for RA have shown that TL1A-DR3 interaction is critical for the pathogenesis of this disease.

The roles of the TL1A pathway in mediating inflammation and autoimmune disorders render it an attractive target for intervention. Blocking of TL1A binding to its endogenous DR3 receptor may lead to the abolishment of downstream signaling effects and thus prevent various inflammatory disorders.

There exists a long-felt need for more effective means of treating or ameliorating inflammatory or autoimmune diseases. The development of agents capable of inhibition of TL1A induced IFN-γ secretion is therefore desirable.

SUMMARY OF THE INVENTION

The present invention provides, in some embodiment thereof, death-domain receptor 3 (DR3) variants, and pharmaceutical compositions comprising same. In some embodiments, the variants and compositions of the invention are effective in reducing TL1A-induced IFN-γ secretion. In some embodiments, the DR3 variants of the invention are useful for treating or ameliorating an autoimmune and/or inflammatory disease or disorder.

The invention is based in part on the unexpected finding that DR3 variants comprising site specific amino acid modifications (e.g., substitutions) as disclosed herein, have increased binding affinity to TL1A. As such, an exemplary peptide exhibited 5-fold increased TL1A binding affinity relative to wild type (WT) DR3. Surprisingly, the DR3 variants were highly effective in inhibiting TL1A induced IFN-γ secretion.

According to one aspect, the invention provides an amino acid molecule comprising the amino acid of SEQ ID NO: 13 (GGTRSPRCDCAGDFHKKIGLFCCRGCPA-GHYLKAPCTEPCGNSTCLVCPQDTFLAWENH HNSE-CARCQACDEQASQVALENCSAVADTRCGCKPGW-FVECQVSQCVSSSPFYCQPCL DCGALHRHTRLLCSRRDTDCGTCLPYEH-GDGCVSCPTSTLCPERCAAVCGWRQMF), or an analogue or a fragment thereof, wherein said amino acid molecule comprises at least one amino acid substitution at a position selected from the group consisting of: H15, 118, E38, V47, D51, W56, N61, A65, K93, Q101, Q104 and L129.

In one embodiment, the amino acid molecule comprises the amino acid of SEQ ID NO: 1: GGTRSPRCDCAGDF$X_1$KK$X_2$GLFCCRGCPAGHYLK-APCT$X_3$PCGNSTCL$X_4$CPQ$X_5$TFLA$X_6$ENHH$X_7$SEC$X_8$-RCQACDEQASQVALENCSAVADTRCGC$X_9$PGWFVE-C$X_{10}$VS$X_{11}$CVSSSPF YCQPCLDCGALHRHTRL$X_{12}$C-SRRDTDCGTCLPGFYEHGDGCVSCPTSTLGSCPER-CAAV CGWRQMF; wherein: $X_1$ is H or Q; $X_2$ is I, T or Y; $X_3$ is E or K; $X_4$ is V or P; $X_5$ is D or G; $X_6$ is W or R; $X_7$ is N or E; $X_8$ is A or T; $X_9$ is K, E or A; $X_{10}$ is Q or S; $X_{11}$ is Q or P; and $X_{12}$ is L or P.

According to some embodiments, the amino acid molecule comprises the amino acid sequence selected from the group consisting of SEQ ID NO: 2-9. According to another embodiment, the amino acid molecule comprises the amino acid of SEQ ID NO: 2. According to another embodiment, the amino acid molecule comprises the amino acid of SEQ ID NO: 3. According to another embodiment, the amino acid molecule comprises the amino acid of SEQ ID NO: 4. According to another embodiment, the amino acid molecule comprises the amino acid of SEQ ID NO: 5. According to another embodiment, the amino acid molecule comprises the amino acid of SEQ ID NO: 6. According to another embodiment, the amino acid molecule comprises the amino acid of SEQ ID NO: 7. According to another embodiment, the amino acid molecule comprises the amino acid of SEQ ID NO: 8. According to another embodiment, the amino acid molecule comprises the amino acid of SEQ ID NO: 9.

According to another embodiment, the amino acid molecule further comprises a peptide of the Fragment crystallizable (Fc) region of an antibody. According to another embodiment, said peptide of the Fragment crystallizable (Fc) region of an antibody comprises the amino acid sequence of SEQ ID NO: 10.

According to another embodiment, the amino acid molecule further comprises a linker comprising the amino acid sequence of SEQ ID NO: 11(IEGRMDRS), wherein said linker is fused to the carboxy terminus of said amino acid of SEQ ID NO: 1 and to the amino terminus of said peptide of the Fc region of an antibody.

According to another aspect, there is provided a composition comprising the amino acid molecule of the invention and a carrier.

According to another aspect, there is provided a polynucleotide molecule comprising a coding portion encoding an amino acid molecule comprising SEQ ID NO: 1. According to another aspect, there is provided an expression vector comprising a polynucleotide molecule comprising a coding portion encoding an amino acid molecule comprising SEQ ID NO: 1. In another embodiment, there is provided an expression vector comprising a polynucleotide molecule comprising the nucleic acid sequence as set forth in SEQ ID NO: 12. According to another aspect, there is provided a cell comprising the expression vector of the invention.

According to another aspect, there is provided a composition comprising the expression vector of the invention and a carrier.

According to another aspect, there is provided a method for reducing or inhibiting inflammation, an immune response, or both in a subject in need thereof, comprising the step of administering to said subject an effective amount of the amino acid molecule of the invention or the composition comprising said amino acid molecule, thereby inhibiting inflammation, an immune response, or both in said subject.

According to another embodiment, said reducing or inhibiting inflammation, an immune response, or both is reducing or inhibiting TL1A-induced IFN-γ secretion in said subject. According to another embodiment, said subject is afflicted with inflammatory bowel disease. According to another embodiment, said subject is afflicted with psoriasis. According to another embodiment, said subject is afflicted with an autoimmune disease. According to another embodiment, said subject is afflicted with asthma. According to another embodiment, said subject is afflicted with arthritis.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIGS. 2A-B. (A) Alignment of mammalian DR3 proteins identifies residues that deviate from the family consensus. Highlighted are V44, D48 and W53 in human DR3 that deviates from the family consensus. (B) The oligonucleotide spiking process for obtaining back-to-consensus mutations in the DR3 gene.

DETAILED DESCRIPTION OF THE INVENTION

Figure 1:
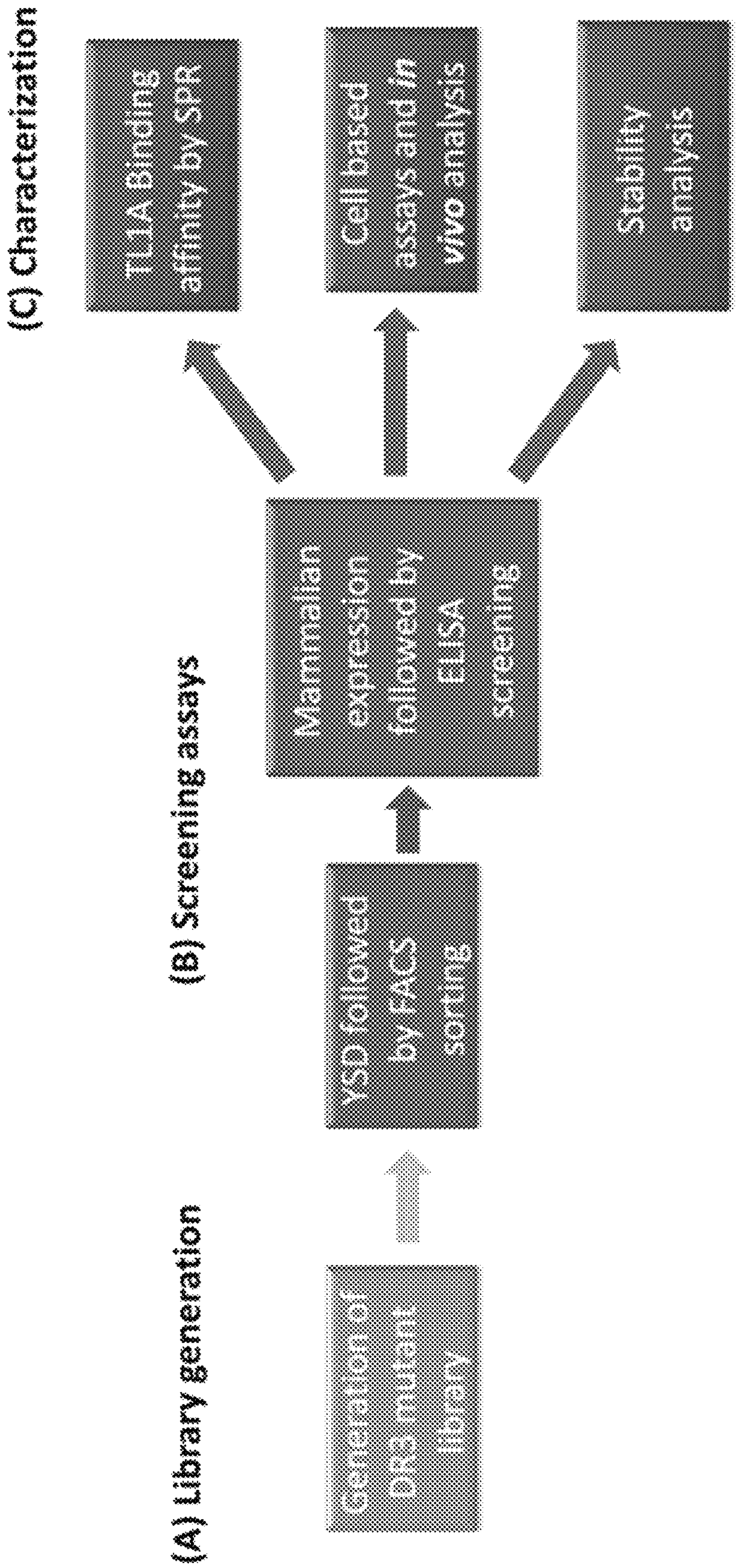
FIG. 1. A diagram of the directed evolution process for the generation of DR3 mutants with improved TL1A affinity, stability and biological activity comprises: (A) library generation, (B) screening, and (C) characterization.

The present invention provides, in some embodiments, polypeptides comprising variants of death-domain receptor 3 (DR3), particularly polypeptides comprising at least one site specific amino acid modification (e.g., substitution), and pharmaceutical compositions comprising same. In some embodiments, the peptides of the invention are effective in preventing, treating or ameliorating autoimmune and/or inflammatory disease.

As exemplified herein below, the soluble DR3 variants bind TL1A with high affinity, thereby preventing ligand binding to the endogenous receptor. Without wishing to be bound to any mechanism of action, use of soluble DR3 receptor is advantageous due to the small molecular weight of the DR3 extracellular ligand binding domain and its perfect recognition of TL1A's binding surface. In additional embodiments, DR3 variants having increased stability and affinity to TL1A increases the ability of the DR3 variants to compete with the endogenous DR3 receptor leading to increased biological activity and serum half-life, following administration.

According to some embodiments, the invention provide a method for reducing or inhibiting inflammation, an immune response, or both, in a subject in need thereof, comprising the step of administering to said subject a composition comprising an effective amount of the amino acid molecule of the invention, thereby reducing or inhibiting inflammation, an immune response, or both in said subject. In other embodiments the method of the invention is useful for treating a T cell-mediated disease, particularly a Th1 cell-mediated disease.

According to another embodiment, said inflammatory disease, includes but is not limited to inflammatory or allergic diseases such as asthma, hypersensitivity lung diseases, hypersensitivity pneumonitis, delayed-type hypersensitivity, interstitial lung disease (ILD) (e.g., idiopathic pulmonary fibrosis, or ILD associated with rheumatoid arthritis or other inflammatory diseases); scleroderma; psoriasis (including T-cell mediated psoriasis); dermatitis (including atopic dermatitis and eczematous dermatitis), iritis, conjunctivitis, keratoconjunctivitis, cutaneous lupus erythematosus, scleroderma, vaginitis, proctitis, drug eruptions, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Graves ophthalmopathy and primary biliary cirrhosis. Each possibility represents a separate embodiment of the present invention.

In other embodiments, the composition is useful for treating an autoimmune disease, including but not limited to: multiple sclerosis (MS), autoimmune neuritis, systemic lupus erythematosus (SLE), psoriasis, Type I diabetes (IDDM), Sjogren's disease, thyroid disease, myasthenia gravis, sarcoidosis, autoimmune uveitis, inflammatory bowel disease (Crohn's and ulcerative colitis), atherosclerosis, primary biliary cirrhosis (PBC), or autoimmune hepatitis, rheumatoid arthritis. Each possibility represents a separate embodiment of the present invention.

In other embodiments, the composition is useful for treating graft rejection, including allograft rejection or graft-versus-host disease.

According to another embodiment, said reducing or inhibiting inflammation, an immune response, or both is inhibiting TL1A-mediated disease.

According to another embodiment, said reducing or inhibiting inflammation, an immune response, or both is inhibiting TL1A-induced IFN-γ secretion in said subject. The term "reducing inflammation" as used herein, refer to a statistically significant reduction in inflammation.

According to another embodiment, said subject is afflicted with inflammatory bowel disease. According to another embodiment, said subject is afflicted with psoriasis. According to another embodiment, said subject is afflicted with an autoimmune disease. According to another embodiment, said subject is afflicted with asthma. According to another embodiment, said subject is afflicted with arthritis. According to another embodiment, said subject is afflicted with colitis.

According to some embodiments, the DR3 variant of the invention comprises the amino acid of SEQ ID NO: 13 (GGTRSPRCDCAGDFHKKIGLFCCRGCPA-GHYLKAPCTEPCGNSTCLVCPQDTFLAWENH HNSE-CARCQACDEQASQVALENCSAVADTRCGCKPGW-FVECQVSQCVSSSPFYCQPCL DCGALHRHTRLLCSRRDTDCGTCLPGFYEH-GDGCVSCPTSTLGSCPERCAAVCGWRQMF), or an analogue or a fragment thereof, wherein the amino acid molecule comprises at least one amino acid substitution at a position selected from the group consisting of: H15, 118, E38, V47, D51, W56, N61, A65, K93, Q101, Q104 and L129. In one embodiment the amino acid molecule of SEQ ID NO: 13 or an analogue or a fragment thereof, comprises at least 2, or alternatively at least 3, or alternatively at least 4, or alternatively at least 5, or alternatively at least 6, or alternatively at least 7, or alternatively at least 8, or alternatively at least 9, or alternatively at least 10, or alternatively at least 11, or alternatively at least 12 amino acids substitutions at positions selected from the group consisting of: H15, 118, E34, E38, V47, D51, W56, N61, A65, K93, Q101, Q104 and L129.

According to some embodiments, the DR3 variant of the invention comprises the amino acid of SEQ ID NO: 1: GGTRSPRCDCAGDFX$_1$KKX$_2$GLFCCRGCPAGHYLK-APCTX$_3$PCGNSTCLX$_4$CPQX$_5$TFLAX$_6$ENHHX$_7$SEC-X$_8$RCQACDEQASQVALENCSAVADTRCGCX$_9$PGW-FVECX$_{10}$VSX$_{11}$CVSSSPF YCQPCLDCGA-LHRHTRLX$_{12}$CSRRDTDCGTCLPGFYEHGDGCVSCP-TSTLGSCPERCAAV CGWRQMF; wherein: X$_1$ is H or Q; X$_2$ is I, T or Y; X$_3$ is E or K; X$_4$ is V or P; X$_5$ is D or G; X$_6$ is W or R; X$_7$ is N or E; X$_8$ is A or T; X$_9$ is K, E or A; X$_{10}$ is Q or S; X$_{11}$ is Q or P; and X$_{12}$ is L or P.

According to some embodiments, the amino acid molecule comprises the amino acid sequence of SEQ ID NO: 4, and optionally at least one amino acid substitution selected from the group consisting of: substitution of Val (V) at position 47 of DR3 to Pro (P); substitution of Asn (N) at position 61 to Glu (E); and substitution of Gln (Q) at position 104 to Pro (P), wherein each possibility represents a separate embodiment of the invention.

The terms "DR3 variants" and "DR3 mutants" are interchangeably used to refer to a nucleic acid and/or nucleotide sequences of DR3 comprising one or more substitutions. It should be appreciated that the wild type sequence of DR3 ECD (e.g., SEQ ID NO: 13) or fragments thereof, are not included under the scope of the present invention.

According to an embodiment of the invention, the DR3 variant of the invention has increased selectively to TL1A. As used herein, the term "selectively" refers to having a binding affinity to TL1A that is substantially greater than said binding affinity for wild-type (WT) TL1A. As used in connection with selective binding affinity, "substantially greater" means at least a 1.5-fold, at least a two-fold, at least a three-fold, at least a four-fold or at least a five-fold increase in the selectivity to a TL1A.

In some embodiments, the DR3 variants of the invention exhibit increased stability of the binding activity in varying temperatures (e.g., at least 25° C., at least 40° C., at least 41° C., at least 42° C., at least 43° C., at least 44° C., at least 45° C., at least 46° C., at least 47° C., at least 48° C., at least 49° C., at least 50° C., at least 51° C. or at least 52° C.) as compared to DR3 WT. As used herein, the term "increased stability" refers to having stability substantially greater than the stability of DR3 WT. In some embodiment, said increased stability is at least a two-fold, at least a three-fold, at least a four-fold, at least a five-fold or at least a six-fold increase in the stability compared to DR3 WT.

In some embodiments, the DR3 variants have increased potency than DR3 WT in inhibiting TL1A induced secretion of IFN-γ. As used herein, the term "increased potency" refers to having potency substantially greater than the potency of DR3 WT. In some embodiment, said increased potency is at least a two-fold, at least a three-fold, at least a four-fold, at least a five-fold or at least a six-fold increase in the potency compared to DR3 WT.

In some embodiments, the DR3 variants reduce the TL1A mediated secretion of anti-inflammatory cytokines (e.g., IL-13 and IL-5). In some embodiment, said reduction is at least a 10%, at least a 20%, at least 30%, at least 40%, at least 50%, at least 55%, at least 60%, at least 65%, or at least 70% reduction in TL1A mediated secretion of anti-inflammatory cytokines.

The term "peptide" as used herein encompasses native peptides (degradation products, synthetic peptides or recombinant peptides), peptidomimetics (typically including non peptide bonds or other synthetic modifications) and the peptide analogues peptoids and semipeptoids, and may have, for example, modifications rendering the peptides more stable while in the body or more capable of penetrating into cells.

The terms "polypeptide", "amino acid molecule" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers.

The term "isolated" peptide refers to a peptide that is essentially free from contaminating cellular components, such as carbohydrate, lipid, or other proteinaceous impurities associated with the peptide in nature. Typically, a preparation of isolated peptide contains the peptide in a highly purified form, i.e., at least about 80% pure, at least about 90% pure, at least about 95% pure, greater than 95% pure, or greater than 99% pure. Each possibility represents a separate embodiment of the present invention.

The present invention further provides fragments, analogs and chemical modifications of the DR3 variants of the present invention as long as they are capable of binding TL1A and/or modulating (e.g. reducing or inhibiting) TL1A induced IFN-γ secretion.

The peptides may comprise additional amino acids, either at the peptide's N-terminus, at the peptide's C-terminus or both. According to another embodiment, the amino acid molecule further comprises a peptide of the Fragment crystallizable (Fc) region of an antibody. According to another embodiment, said peptide of the Fc region of an antibody comprises the amino acid sequence of SEQ ID NO: 10. According to another embodiment, the amino acid molecule further comprises a linker between the amino acid molecule and the Fc region. Said linker, in some embodiments, has a length of no more than 20 amino acids, no more than 19 amino acids, no more than 18 amino acids, no more than 17 amino acids, no more than 16 amino acids, no more than 15 amino acids, no more than 14 amino acids, no more than 13 amino acids or no more than 12 amino acids, no more than 11 amino acids, no more than 10 amino acids, no more than 9 amino acids, no more than 8 amino acids, no more than 7 amino acids, no more than 6 amino acids, no more than 5 amino acids, no more than 4 amino acids, no more than 3 amino acids, no more than 2 amino acids or of one amino acid. In some embodiments, the linker comprises the amino acid sequence of SEQ ID NO: 11(IEGRMDRS). In exemplified embodiments, said linker is fused to the carboxy terminus of said amino acid of SEQ ID NO: 1 and to the amino terminus of said peptide of the Fc region.

Conservative substitutions of amino acids as known to those skilled in the art are within the scope of the present invention. Conservative amino acid substitutions includes replacement of one amino acid with another having the same type of functional group or side chain e.g. aliphatic, aromatic, positively charged, negatively charged. One of skill will recognize that individual substitutions, deletions or additions to peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art.

The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W) (see, e.g., Creighton, Proteins, 1984).

The term "analog" includes any peptide having an amino acid sequence substantially identical to one of the sequences specifically shown herein in which one or more residues have been conservatively substituted with a functionally similar residue and which displays the abilities as described herein. Examples of conservative substitutions include the substitution of one non-polar (hydrophobic) residue such as isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. Each possibility represents a separate embodiment of the present invention.

The phrase "conservative substitution" also includes the use of a chemically derivatized residue in place of a non-derivatized residue provided that such peptide displays the requisite function of modulating the immune system's innate response as specified herein.

The term "derived from" or "corresponding to" refers to construction of an amino acid sequence based on the knowledge of a sequence using any one of the suitable means known to one skilled in the art, e.g. chemical synthesis in accordance with standard protocols in the art.

According to another embodiment, the DR3 variant of the invention has at least 75% sequence identity to any one of SEQ ID NO: 1-9. According to another embodiment, said DR3 variant has at least 80% sequence identity to any one of SEQ ID NO: 1-9. According to another embodiment, said DR3 variant has at least 85% sequence identity to any one of SEQ ID NO: 1-9. According to another embodiment, said DR3 variant has at least 90% sequence identity to any one of SEQ ID NO: 1-9. According to another embodiment, said DR3 variant has at least 95% sequence identity to any one of SEQ ID NO: 1-9.

Percentage sequence identity can be determined, for example, by the Fitch et al. version of the algorithm (Fitch et al, Proc. Natl. Acad. Sci. U.S.A. 80: 1382-1386 (1983)) described by Needleman et al, (Needleman et al, J. Mol. Biol. 48: 443-453 (1970)), after aligning the sequences to provide for maximum homology. Alternatively, the determination of percent identity between two sequences can be accomplished using the mathematical algorithm of Karlin and Altschul (1993) Proc. Natl. Acad. Sci. USA 90:5873-5877. Such an algorithm is incorporated into the BLASTP program of Altschul et al. (1990) J. Mol. Biol. 215, 403-410. BLAST protein searches are performed with the BLASTP program to obtain amino acid sequences homologous to SEQ ID NO: 4. In order to obtain gapped alignments for comparative purposes, Gapped BLAST is utilized as described in Altschul et al (1997) Nucleic Acids Res. 25:3389-3402. When utilizing BLAST and Gapped BLAST programs, the default parameters of the respective programs (e.g.,)(BLAST) are used.

Typically, the present invention encompasses derivatives of the DR3 peptides. The term "derivative" or "chemical derivative" includes any chemical derivative of the peptide having one or more residues chemically derivatized by reaction of side chains or functional groups. Such derivatized molecules include, for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those peptides, which contain one or more naturally occurring amino acid derivatives of the twenty standard amino acid residues. For example: 4-hydroxyproline may be substituted for proline; 5-hydroxylysine may be substituted for lysine; 3-methylhistidine may be substituted for histidine; homoserine may be substituted or serine; and ornithine may be substituted for lysine.

In addition, a peptide derivative can differ from the natural sequence of the peptides of the invention by chemical modifications including, but are not limited to, terminal-NH2 acylation, acetylation, or thioglycolic acid amidation, and by terminal-carboxlyamidation, e.g., with ammonia, methylamine, and the like. Peptides can be either linear, cyclic or branched and the like, which conformations can be achieved using methods well known in the art.

The peptide derivatives and analogs according to the principles of the present invention can also include side chain bond modifications, including but not limited to —CH2-NH—, —CH2-S—, —CH2-S=0, OC—NH—, —CH2-O—, —CH2-CH2-, S=C—NH—, and —CH=CH—, and backbone modifications such as modified peptide bonds. Peptide bonds (—CO—NH—) within the peptide can be substituted, for example, by N-methylated bonds (—N(CH3)-CO—); ester bonds (—C(R)H—C-0-0-C(R)H—N); ketomethylene bonds (—CO—CH2-); a-aza bonds (—NH—N(R)—CO—), wherein R is any alkyl group, e.g., methyl; carba bonds (—CH2-NH—); hydroxyethylene bonds (—CH(OH)—CH2-); thioamide bonds (—CS—NH); olefmic double bonds (—CH=CH—); and peptide derivatives (—N(R)—CH2-CO—), wherein R is the "normal" side chain, naturally presented on the carbon atom. These modifications can occur at one or more of the bonds along the peptide chain and even at several (e.g., 2-3) at the same time.

The present invention also encompasses peptide derivatives and analogs in which free amino groups have been derivatized to form amine hydrochlorides, p-toluene sulfonylamino groups, carbobenzoxyamino groups, t-butyloxycarbonylamino groups, chloroacetylamino groups or formylamino groups. Free carboxyl groups may be derivatized to form, for example, salts, methyl and ethyl esters or other types of esters or hydrazides. The imidazole nitrogen of histidine can be derivatized to form N-im-benzylhistidine.

The peptide analogs can also contain non-natural amino acids. Examples of non-natural amino acids include, but are not limited to, sarcosine (Sar), norleucine, ornithine, citrulline, diaminobutyric acid, homoserine, isopropyl Lys, 3-(2'-naphtyl)-Ala, nicotinyl Lys, amino isobutyric acid, and 3-(3'-pyridyl-Ala).

Furthermore, the peptide analogs can contain other derivatized amino acid residues including, but not limited to, methylated amino acids, N-benzylated amino acids, O-benzylated amino acids, N-acetylated amino acids, O-acetylated amino acids, carbobenzoxy-substituted amino acids and the like. Specific examples include, but are not limited to, methyl-Ala (Me Ala), MeTyr, MeArg, MeGlu, MeVal, MeHis, N-acetyl-Lys, O-acetyl-Lys, carbobenzoxy-Lys, Tyr-O-Benzyl, Glu-O-Benzyl, Benzyl-His, Arg-Tosyl, t-butylglycine, t-butylalanine, phenylglycine, cyclohexylalanine, and the like.

The invention further includes peptide analogs, which can contain one or more D-isomer forms of the amino acids.

Production of retro-inverso D-amino acid peptides where at least one amino acid, and perhaps all amino acids are D-amino acids is well known in the art. When all of the amino acids in the peptide are D-amino acids, and the N- and C-terminals of the molecule are reversed, the result is a molecule having the same structural groups being at the same positions as in the L-amino acid form of the molecule. However, the molecule is more stable to proteolytic degradation and is therefore useful in many of the applications recited herein. Diastereomeric peptides may be highly advantageous over all L- or all D-amino acid peptides having the same amino acid sequence because of their higher water solubility, lower immunogenicity, and lower susceptibility to proteolytic degradation. The term "diastereomeric peptide" as used herein refers to a peptide comprising both L-amino acid residues and D-amino acid residues. The number and position of D-amino acid residues in a diastereomeric peptide of the preset invention may be variable so long as the peptide is capable of displaying the requisite function binding TL1A and/or modulating (e.g. reducing or inhibiting) TL1A induced IFN-γ secretion, as specified herein.

The peptides of the invention may be synthesized or prepared by techniques well known in the art. The peptides can be synthesized by a solid phase peptide synthesis method of Merrifield (see J. Am. Chem. Soc, 85:2149, 1964). Alternatively, the peptides of the present invention can be synthesized using standard solution methods well known in the art (see, for example, Bodanszky, M., Principles of Peptide Synthesis, Springer-Verlag, 1984) or by any other method known in the art for peptide synthesis.

In general, these methods comprise sequential addition of one or more amino acids or suitably protected amino acids to a growing peptide chain bound to a suitable resin.

Normally, either the amino or carboxyl group of the first amino acid is protected by a suitable protecting group. The protected or derivatized amino acid can then be either attached to an inert solid support (resin) or utilized in solution by adding the next amino acid in the sequence having the complimentary (amino or carboxyl) group suitably protected, under conditions conductive for forming the amide linkage. The protecting group is then removed from this newly added amino acid residue and the next amino acid (suitably protected) is added, and so forth. After all the desired amino acids have been linked in the proper sequence, any remaining protecting groups are removed sequentially or concurrently, and the peptide chain, if synthesized by the solid phase method, is cleaved from the solid support to afford the final peptide.

In the solid phase peptide synthesis method, the alpha-amino group of the amino acid is protected by an acid or base sensitive group. Such protecting groups should have the properties of being stable to the conditions of peptide linkage formation, while being readily removable without destruction of the growing peptide chain. Suitable protecting groups are t-butyloxycarbonyl (BOC), benzyloxycarbonyl (Cbz), biphenylisopropyloxycarbonyl, t-amyloxycarbonyl, isobornyloxycarbonyl, (alpha, alpha)-dimethyl-3,5dimethoxybenzyloxycarbonyl, o-nitrophenylsulfenyl, 2-cyano-t-butyloxycarbonyl, 9-fluorenylmethyloxycarbonyl (FMOC) and the like.

In the solid phase peptide synthesis method, the C-terminal amino acid is attached to a suitable solid support. Suitable solid supports useful for the above synthesis are those materials, which are inert to the reagents and reaction conditions of the stepwise condensation-deprotection reactions, as well as being insoluble in the solvent media used. Suitable solid supports are chloromethylpolystyrene-divinylbenzene polymer, hydroxymethyl-polystyrene-divinylbenzene polymer, and the like. The coupling reaction is accomplished in a solvent such as ethanol, acetonitrile, N,N-dimethylformamide (DMF), and the like. The coupling of successive protected amino acids can be carried out in an automatic polypeptide synthesizer as is well known in the art.

The peptides of the invention may alternatively be synthesized such that one or more of the bonds, which link the amino acid residues of the peptides are non-peptide bonds. These alternative non-peptide bonds include, but are not limited to, imino, ester, hydrazide, semicarbazide, and azo bonds, which can be formed by reactions well known to skilled in the art.

In some embodiments, recombinant protein techniques are used to generate the protein of the invention. In some embodiments, recombinant protein techniques are used for generation of relatively long peptides (e.g., longer than 18-25 amino acids). In some embodiments, recombinant protein techniques are used for the generation of large amounts of the protein of the invention. In some embodiments, recombinant techniques are described by Bitter et al., (1987) Methods in Enzymol. 153:516-544, Studier et al. (1990) Methods in Enzymol. 185:60-89, Brisson et al. (1984) Nature 310:511-514, Takamatsu et al. (1987) EMBO J. 6:307-311, Coruzzi et al. (1984) EMBO J. 3:1671-1680 and Brogli et al, (1984) Science 224:838-843, Gurley et al. (1986) Mol. Cell. Biol. 6:559-565 and Weissbach & Weissbach, 1988, Methods for Plant Molecular Biology, Academic Press, NY, Section VIII, pp 421-463.

The peptides of the present invention, analogs or derivatives thereof produced by recombinant techniques can be purified so that the peptides will be substantially pure when administered to a subject. The term "substantially pure" refers to a compound, e.g., a peptide, which has been separated from components, which naturally accompany it.

Typically, a peptide is substantially pure when at least 50%, preferably at least 75%, more preferably at least 90%, and most preferably at least 99% of the total material (by volume, by wet or dry weight, or by mole percent or mole fraction) in a sample is the peptide of interest. Purity can be measured by any appropriate method, e.g., in the case of peptides by HPLC analysis.

According to another aspect, the present invention provides an isolated polynucleotide sequence encoding the polypeptides of the present invention, or an analog or a conjugate thereof. A non-limiting example of a polynucleotide sequence encoding DR3 ECD fused to an Fc region comprises the nucleic acid sequence of SEQ ID NO: 12. It is within the capabilities of a skilled artisan to generate the DRS mutants of the invention based on SEQ ID NO: 12.

The term "polynucleotide" means a polymer of deoxyribonucleic acid (DNA), ribonucleic acid (RNA) or a combination thereof, which can be derived from any source, can be single-stranded or double-stranded, and can optionally contain synthetic, non-natural, or altered nucleotides, which are capable of being incorporated into DNA or RNA polymers.

An "isolated polynucleotide" refers to a polynucleotide segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term also applies to polynucleotides, which have been substantially purified from other components, which naturally accompany the polynucleotide in the cell, e.g., RNA or DNA or proteins. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence, and RNA such as mRNA.

The term "encoding" refers to the inherent property of specific sequences of nucleotides in an isolated polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a peptide or protein if transcription and translation of mRNA corresponding to that gene produces the peptide or protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the peptide or protein or other product of that gene or cDNA.

One who is skilled in the art will appreciate that more than one polynucleotide may encode any given peptide or protein in view of the degeneracy of the genetic code and the allowance of exceptions to classical base pairing in the third position of the codon, as given by the so-called "Wobble rules." It is intended that the present invention encompass polynucleotides that encode the peptides of the present invention as well as any analog thereof.

A polynucleotide of the present invention can be expressed as a secreted peptide where the polypeptide of the present invention or analog thereof is isolated from the medium in which the host cell containing the polynucleotide is grown, or the polynucleotide can be expressed as an intracellular polypeptide by deleting the leader or other peptides, in which case the polypeptide of the present invention or analog thereof is isolated from the host cells. The polypeptides of the present invention or analog thereof are then purified by standard protein purification methods known in the art.

The polypeptide of the present invention, analogs, or derivatives thereof can also be provided to the tissue of interest by transferring an expression vector comprising an isolated polynucleotide encoding the polypeptide of the present invention, or analog thereof to cells associated with the tissue of interest. The cells produce the peptide such that it is suitably provided to the cells within the tissue to exert a biological activity such as, for example, to reduce or inhibit inflammatory processes within the tissue of interest.

The expression vector according to the principles of the present invention further comprises a promoter. In the context of the present invention, the promoter must be able to drive the expression of the peptide within the cells. Many viral promoters are appropriate for use in such an expression vector (e.g., retroviral ITRs, LTRs, immediate early viral promoters (IEp) (such as herpes virus IEp (e.g., ICP4-IEp and ICPO-IEp) and cytomegalovirus (CMV) IEp), and other viral promoters (e.g., late viral promoters, latency-active promoters (LAPs), Rous Sarcoma Virus (RSV) promoters, and Murine Leukemia Virus (MLV) promoters). Other suitable promoters are eukaryotic promoters, which contain enhancer sequences (e.g., the rabbit β-globin regulatory elements), constitutively active promoters (e.g., the β-actin promoter, etc.), signal and/or tissue specific promoters (e.g., inducible and/or repressible promoters, such as a promoter responsive to TNF or RU486, the metallothionine promoter, etc.), and tumor-specific promoters.

Within the expression vector, the polynucleotide encoding the polypeptide of the present invention, or analog thereof and the promoter are operably linked such that the promoter is able to drive the expression of the polynucleotide. As long as this operable linkage is maintained, the expression vector can include more than one gene, such as multiple genes separated by internal ribosome entry sites (IRES). Furthermore, the expression vector can optionally include other elements, such as splice sites, polyadenylation sequences, transcriptional regulatory elements (e.g., enhancers, silencers, etc.), or other sequences.

The expression vectors are introduced into the cells in a manner such that they are capable of expressing the isolated polynucleotide encoding the polypeptide of the present invention or analog thereof contained therein. Any suitable vector can be so employed, many of which are known in the art. Examples of such vectors include naked DNA vectors (such as oligonucleotides or plasmids), viral vectors such as adeno-associated viral vectors (Berns et al, 1995, Ann. N.Y. Acad. Sci. 772:95-104, the contents of which are hereby incorporated by reference in their entirety), adenoviral vectors, herpes virus vectors (Fink et al, 1996, Ann. Rev. Neurosci. 19:265-287), packaged amplicons (Federoff et al, 1992, Proc. Natl. Acad. Sci. USA 89: 1636-1640, the contents of which are hereby incorporated by reference in their entirety), papilloma virus vectors, picomavirus vectors, polyoma virus vectors, retroviral vectors, SV40 viral vectors, vaccinia virus vectors, and other vectors. Additionally, the vector can also include other genetic elements, such as, for example, genes encoding a selectable marker (e.g., β-gal or a marker conferring resistance to a toxin), a pharmacologically active protein, a transcription factor, or other biologically active sub stance.

Methods for manipulating a vector comprising an isolated polynucleotide are well known in the art (e.g., Sambrook et al., 1989, Molecular Cloning: A Laboratory Manual, 2d edition, Cold Spring Harbor Press, the contents of which are hereby incorporated by reference in their entirety) and include direct cloning, site specific recombination using recombinases, homologous recombination, and other suitable methods of constructing a recombinant vector. In this manner, an expression vector can be constructed such that it can be replicated in any desired cell, expressed in any desired cell, and can even become integrated into the genome of any desired cell.

The expression vector comprising the polynucleotide of interest is introduced into the cells by any means appropriate for the transfer of DNA into cells. Many such methods are well known in the art (e.g., Sambrook et al, supra; see also Watson et al, 1992, Recombinant DNA, Chapter 12, 2d edition, Scientific American Books, the contents of which are hereby incorporated by reference in their entirety). Thus, in the case of prokaryotic cells, vector introduction can be accomplished, for example, by electroporation, transformation, transduction, conjugation, or mobilization. For eukaryotic cells, vectors can be introduced through the use of, for example, electroporation, transfection, infection, DNA coated microprojectiles, or protoplast fusion. Examples of eukaryotic cells into which the expression vector can be introduced include, but are not limited to, ovum, stem cells, blastocytes, and the like.

Cells, into which the polynucleotide has been transferred under the control of an inducible promoter if necessary, can be used as transient transformants. Such cells themselves may then be transferred into a subject for therapeutic benefit therein. Thus, the cells can be transferred to a site in the subject such that the peptide of the invention is expressed therein and secreted therefrom and thus reduces or inhibits, for example, T cell mediated processes so that the clinical condition of the subject is improved. Alternatively, particularly in the case of cells to which the vector has been added in vitro, the cells can first be subjected to several rounds of clonal selection (facilitated usually by the use of a selectable marker sequence in the vector) to select for stable transformants. Such stable transformants are then transferred to a subject, preferably a human, for therapeutic benefit therein.

Within the cells, the polynucleotide encoding the peptides of the present invention, or analog thereof is expressed, and optionally is secreted. Successful expression of the polynucleotide can be assessed using standard molecular biology techniques (e.g., Northern hybridization, Western blotting, immunoprecipitation, enzyme immunoassay, etc.).

The present invention encompasses transgenic animals comprising an isolated polynucleotide encoding the peptides of the invention.

Pharmaceutical Compositions of the Invention

In some embodiments, there is provided compositions (i.e., pharmaceutical compositions) comprising as an active ingredient a therapeutically effective amount of an amino acid molecule (i.e., polypeptides) of the present invention (e.g., SEQ ID NO: 1), and a pharmaceutically acceptable carrier.

The pharmaceutical compositions of the invention can be formulated in the form of a pharmaceutically acceptable salt of the polypeptides of the invention or their analogs, or derivatives thereof. Pharmaceutically acceptable salts include those salts formed with free amino groups such as salts derived from non-toxic inorganic or organic acids such as hydrochloric, phosphoric, acetic, oxalic, tartaric acids, and the like, and those salts formed with free carboxyl groups such as salts derived from non-toxic inorganic or organic bases such as sodium, potassium, ammonium, calcium, ferric hydroxides, isopropylamine, triethylamine, 2-ethylamino ethanol, histidine, procaine, and the like. In one embodiment, pharmaceutical compositions of the present invention are manufactured by processes well known in the art, e.g., by means of conventional mixing, dissolving, granulating, dragee-making, levigating, emulsifying, encapsulating, entrapping or lyophilizing processes.

The term "pharmaceutically acceptable" means suitable for administration to a subject, e.g., a human. For example, the term "pharmaceutically acceptable" can mean approved by a regulatory agency of the Federal or a state government or listed in the U. S. Pharmacopeia or other generally recognized pharmacopeia for use in animals, and more particularly in humans. The term "carrier" refers to a diluent, adjuvant, excipient, or vehicle with which the therapeutic compound is administered. Such pharmaceutical carriers can be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; and agents for the adjustment of tonicity such as sodium chloride or dextrose are also envisioned.

The compositions can take the form of solutions, suspensions, emulsions, tablets, pills, capsules, powders, gels, creams, ointments, foams, pastes, sustained-release formulations and the like. The compositions can be formulated as a suppository, with traditional binders and carriers such as triglycerides, microcrystalline cellulose, gum tragacanth or gelatin. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in: Remington's Pharmaceutical Sciences" by E. W. Martin, the contents of which are hereby incorporated by reference herein. Such compositions will contain a therapeutically effective amount of the peptide of the invention, preferably in a substantially purified form, together with a suitable amount of carrier so as to provide the form for proper administration to the subject.

An embodiment of the invention relates to a polypeptide presented in unit dosage form and are prepared by any of the methods well known in the art of pharmacy. In an embodiment of the invention, the unit dosage form is in the form of a tablet, capsule, lozenge, wafer, patch, ampoule, vial or pre-filled syringe. In addition, in vitro assays may optionally be employed to help identify optimal dosage ranges. The precise dose to be employed in the formulation will also depend on the route of administration, and the nature of the disease or disorder, and should be decided according to the judgment of the practitioner and each patient's circumstances. Effective doses can be extrapolated from dose-response curves derived from in-vitro or in-vivo animal model test bioassays or systems.

Depending on the location of the tissue of interest, the polypeptides of the present invention can be supplied in any manner suitable for the provision of the peptide to cells within the tissue of interest. Thus, for example, a composition containing the polypeptides can be introduced, for example, into the systemic circulation, which will distribute said peptide to the tissue of interest. Alternatively, a composition can be applied topically to the tissue of interest (e.g., injected, or pumped as a continuous infusion, or as a bolus within a tissue, applied to all or a portion of the surface of the skin, etc.).

In an embodiment of the invention, polypeptides are administered via oral, rectal, vaginal, topical, nasal, ophthalmic, transdermal, subcutaneous, intramuscular, intraperitoneal or intravenous routes of administration. The route of administration of the pharmaceutical composition will depend on the disease or condition to be treated. Suitable routes of administration include, but are not limited to, parenteral injections, e.g., intradermal, intravenous, intramuscular, intralesional, subcutaneous, intrathecal, and any other mode of injection as known in the art. Although the bioavailability of peptides administered by other routes can be lower than when administered via parenteral injection, by using appropriate formulations it is envisaged that it will be possible to administer the compositions of the invention via transdermal, oral, rectal, vaginal, topical, nasal, inhalation and ocular modes of treatment. In addition, it may be desirable to introduce the pharmaceutical compositions of the invention by any suitable route, including intraventricular and intrathecal injection; intraventricular injection may be facilitated by an intraventricular catheter, for example, attached to a reservoir. Pulmonary administration can also be employed, e.g., by use of an inhaler or nebulizer.

For topical application, a peptide of the present invention, derivative, analog or a fragment thereof can be combined with a pharmaceutically acceptable carrier so that an effective dosage is delivered, based on the desired activity. The carrier can be in the form of, for example, and not by way of limitation, an ointment, cream, gel, paste, foam, aerosol, suppository, pad or gelled stick.

For oral applications, the pharmaceutical composition may be in the form of tablets or capsules, which can contain any of the following ingredients, or compounds of a similar nature: a binder such as microcrystalline cellulose, gum tragacanth or gelatin; an excipient such as starch or lactose; a disintegrating agent such as alginic acid, Primogel, or corn starch; a lubricant such as magnesium stearate; or a glidant such as colloidal silicon dioxide. When the dosage unit form is a capsule, it can contain, in addition to materials of the above type, a liquid carrier such as fatty oil. In addition, dosage unit forms can contain various other materials which modify the physical form of the dosage unit, for example, coatings of sugar, shellac, or other enteric agents. The tablets of the invention can further be film coated.

For purposes of parenteral administration, solutions in sesame or peanut oil or in aqueous propylene glycol can be employed, as well as sterile aqueous solutions of the corresponding water-soluble salts. Such aqueous solutions may be suitably buffered, if necessary, and the liquid diluent first rendered isotonic with sufficient saline or glucose. These aqueous solutions are especially suitable for intravenous, intramuscular, subcutaneous and intraperitoneal injection purposes.

The compositions of the present invention are generally administered in the form of a pharmaceutical composition comprising at least one of the active components of this invention together with a pharmaceutically acceptable carrier or diluent. Thus, the compositions of this invention can be administered either individually or together in any conventional oral, parenteral or transdermal dosage form.

Pharmaceutical compositions according to embodiments of the invention may contain 0.1%-95% of the active components(s) of this invention, preferably 1%-70%. In any event, the composition or formulation to be administered may contain a quantity of active components according to embodiments of the invention in an amount effective to treat the condition or disease of the subject being treated.

The compositions also comprise preservatives, such as benzalkonium chloride and thimerosal and the like; chelating agents, such as EDTA sodium and others; buffers such as phosphate, citrate and acetate; tonicity agents such as sodium chloride, potassium chloride, glycerin, mannitol and others; antioxidants such as ascorbic acid, acetylcystine, sodium metabisulfote and others; aromatic agents; viscosity adjustors, such as polymers, including cellulose and derivatives thereof; and polyvinyl alcohol and acid and bases to adjust the pH of these aqueous compositions as needed. The compositions may also comprise local anesthetics or other actives.

In addition, the compositions may further comprise binders (e.g. acacia, cornstarch, gelatin, carbomer, ethyl cellulose, guar gum, hydroxypropyl cellulose, hydroxypropyl methyl cellulose, povidone), disintegrating agents (e.g. cornstarch, potato starch, alginic acid, silicon dioxide, croscarmelose sodium, crospovidone, guar gum, sodium starch glycolate), buffers (e.g., Tris-HCl., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants.

The polypeptides of the present invention, derivatives, or analogs thereof can be delivered in a controlled release system. Thus, an infusion pump can be used to administer the peptide such as the one that is used, for example, for delivering insulin or chemotherapy to specific organs or tumors. In one embodiment, the peptide of the invention is administered in combination with a biodegradable, biocompatible polymeric implant, which releases the peptide over a controlled period of time at a selected site. Examples of preferred polymeric materials include, but are not limited to, polyanhydrides, polyorthoesters, polyglycolic acid, polylactic acid, polyethylene vinyl acetate, copolymers and blends thereof (See, Medical applications of controlled release, Langer and Wise (eds.), 1974, CRC Pres., Boca Raton, Fla., the contents of which are hereby incorporated by reference in their entirety). In yet another embodiment, a controlled release system can be placed in proximity to a therapeutic target, thus requiring only a fraction of the systemic dose.

In one embodiment, compositions of the present invention are presented in a pack or dispenser device, such as an FDA approved kit, which contain one or more unit dosage forms containing the active ingredient. In one embodiment, the pack or dispenser device is accompanied by instructions for administration.

In one embodiment, it will be appreciated that the polypeptides of the present invention can be provided to the individual with additional active agents to achieve an improved therapeutic effect as compared to treatment with each agent by itself. In another embodiment, measures (e.g., dosing and selection of the complementary agent) are taken to adverse side effects which are associated with combination therapies.

A "therapeutically effective amount" of the peptide is that amount of peptide which is sufficient to provide a beneficial effect to the subject to which the peptide is administered. More specifically, a therapeutically effective amount means an amount of the peptide effective to prevent, alleviate or ameliorate tissue damage or symptoms of a disease of the subject being treated.

In some embodiments, preparation of effective amount or dose can be estimated initially from in vitro assays. In one embodiment, a dose can be formulated in animal models and such information can be used to more accurately determine useful doses in humans.

In one embodiment, toxicity and therapeutic efficacy of the active ingredients described herein can be determined by standard pharmaceutical procedures in vitro, in cell cultures or experimental animals. In one embodiment, the data obtained from these in vitro and cell culture assays and animal studies can be used in formulating a range of dosage for use in human. In one embodiment, the dosages vary depending upon the dosage form employed and the route of administration utilized. In one embodiment, the exact formulation, route of administration and dosage can be chosen by the individual physician in view of the patient's condition. [See e.g., Fingl, et al., (1975) "The Pharmacological Basis of Therapeutics", Ch. 1 p. 1].

In one embodiment, depending on the severity and responsiveness of the condition to be treated, dosing can be of a single or a plurality of administrations, with course of treatment lasting from several days to several weeks or until cure is effected or diminution of the disease state is achieved. In one embodiment, the amount of a composition to be administered will, of course, be dependent on the subject being treated, the severity of the affliction, the manner of administration, the judgment of the prescribing physician, etc. In one embodiment, compositions including the preparation of the present invention formulated in a compatible pharmaceutical carrier are also be prepared, placed in an appropriate container, and labeled for treatment of an indicated condition.

In the discussion unless otherwise stated, adjectives such as "substantially" and "about" modifying a condition or relationship characteristic of a feature or features of an embodiment of the invention, are understood to mean that the condition or characteristic is defined to within tolerances that are acceptable for operation of the embodiment for an application for which it is intended. Unless otherwise indicated, the word "or" in the specification and claims is considered to be the inclusive "or" rather than the exclusive or, and indicates at least one of, or any combination of items it conjoins.

In the description and claims of the present application, each of the verbs, "comprise," "include" and "have" and conjugates thereof, are used to indicate that the object or objects of the verb are not necessarily a complete listing of components, elements or parts of the subject or subjects of the verb.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Strategies for Protein Purification and Characterization—A Laboratory Course Manual" CSHL Press (1996); all of which are incorporated by reference. Other general references are provided throughout this document.

Materials and Methods

Plasmids and Cell Culture

The human DR3 extracellular domain was amplified from EST cDNA clone of human DR3 purchased form Open Biosystems. The *E. coli* E. Cloni strain (Lucigen) was used for cloning and plasmid extraction. For yeast surface display, the variants were cloned into the pCTCON plasmid using the NheI and BamHI sites. For expression in mammalian cells, the pFUSE (Invivogen) vector were used, to yield DR3-ECD variant fused with human IgG1 Fc.

HEK293T were grown in DMEM supplemented with 10% FBS (Biological Industries, Beit-Haemek, Israel), 2 mM Glutamine, 1× Pen/step solution (Biological Industries, Beit-Haemek, Israel), 3 hours prior to transfection the media was exchanged to Freestyle serum free media (Invitrogen). H293F were grown in Freestyle media without any supplement. PBL and CD4+ T cell subset were grown at a concentration of 1*106/ml in RPMI 1640, with 10% FBS 2 mM Glutamine, 1× Pen/strep solution (Biological Industries, Beit-Haemek, Israel) supplemented with 10% heat inactivated FBS (Biological Industries, Beit-Haemek, Israel).

Yeast Surface Display

DR3 variants were displayed on the yeast cell surface of EBY100 strain cells (Chao, G. et al. *Nat Protoc* 1, 755-68, 2006) and analyzed by flow cytometry, essentially as described. Briefly, EBY100 cells transformed with plasmid pCTCON containing the desired clone were grown in SDCAA media (20 g sucrose, 6.7 g yeast nitrogen base, 5 g casamino acids, 5.4 g Na2HPO4 and 8.56 g NaH2PO4*H2O) at 30° C. to logarithmic phase. Then, $2*10^6$ of cells were washed, resuspended in SGCAA induction media (similar to SDCAA but containing galactose instead of sucrose) and grown at 30° C. with shaking for an additional 18 hours. Induced cells ($1*10^6$) were collected by centrifugation, washed with PBSF (PBS+1 g/L BSA) and incubated for 1 hour at 25° C. with 0.2 μM TL1A (R&D Systems) that was biotinylated using biotin labeling kit (Pierce) according to manufacturer's procedure. The cells were then washed and incubated for 1 hour at 25° C. with mouse α-myc antibodies (Santa Cruz Biotechnology, 1 μl/50 PBSF). Subsequently, cells were washed again and incubated with FITC-conjugated α-mouse IgG (Sigma, 1 μl/50 μl PBSF) and allophycocyanin-conjugated streptavidin (Jackson Immunoresearch, 1 μl/50 μl PBSF) for an additional hour on ice, with frequent mixing. The labeled cells were washed, resuspended with PBSF and analyzed by flow cytometry (FACS Calibur, BD).

Library Generation

For the generation of DR3 back-to-consensus library, the human DR3 gene was amplified by PCR, and 5 μg were digested with DNaseI to yield 50-125 bp fragments, as previously described 28. The fragments were reassembled, as in DNA shuffling 31, in the presence of a mixture of 16 short oligonucleotides (4-6 nM each), resulting in a library containing 3-8 mutations in each gene with an average number of mutation of ~4 (Stemmer, W. P., 1994, Proc Natl Acad Sci USA 91, 10747-51; Aharoni et al., 2004, Proceedings of the National Academy of Sciences of the United States of America 101, 482-487). The estimated complexity of the library is ~170,000 mutants based on the following equation: N!/(N−K)!*K, where N is the total number of positions and K is the average number of mutations inserted into the gene (Bamias, G., et al. 2006, Proc Natl Acad Sci USA 103, 8441-6). The reaction mixture was further amplified by nested PCR, as described (Chao, G., et al. 2006, Nat Protoc, 1, 755-68). The libraries were ligated into the pCTCON vector for yeast surface display or cloned by recombination into yeast.

Library Selection Using Yeast Surface Display

The library was induced and labeled with c-myc and biotinylated TL1A, as described above. EBY100 cells ($1*10^7$) displaying the DR3 library were labeled, analyzed and sorted using a FACS (Synergy iCyt). Three iterative rounds of enrichment were performed. In each round, multiple ‘positive’ events ($3\text{-}5*10^4$), corresponding to cells found within the top 1-2% of the green and red fluorescence intensity area, were collected into growth media and plated on agar for a new round of enrichment. For initial sorting of the naïve library, a sorting gate of the top 5% of fluorescent cells was used. Selection rounds were continued until no further enrichment was obtained.

Screening of Enriched DR3 Libraries Using ELISA Following Mammalian Expression

A pool of plasmids from the last round of FACS enrichment was PCR-amplified, cloned into pFUSE plasmid as described above and transformed into the HEK293T cells. Two to three days post transfection the cultured media containing the secreted DR3 variants were tested for DR3-TL1A interaction using ELISA. To conduct the assay ELISA plates (Griener Microlon 96 W) were incubated with 100 μl of 0.66 μg/ml monoclonal mouse α-TL1A antibodies (Santa Cruz) for 1 hour, washed with PBS supplemented with 0.05% Tween-80 (PBST) and 100 μl of 0.6 μg/ml TL1A (Cam Bio) were added to the plate for an additional hour. The plates were then washed with PBST and blocked by incubation with 150 μl of PBS supplemented with 3% skim milk for 1 hour. Following blocking, the plates were washed and incubated with 100 μl of media of HEK293T transfected with WT or DR3 mutants harvested 48 or 72 hours post transfection, ELISA plates were shaken for additional hour. DR3-Fc (R&D Systems) was added at a concentration of 2 μg/ml as a positive control, and PBS supplemented with 1% BSA served as a negative control. Plates were then washed with PBST, incubated with 100 μl of 0.05 μg/ml of biotinylated goat polyclonal α-DR3 antibodies (R&D Systems), followed by incubation with secondary peroxidase-conjugated streptavidin (Jackson, 1:10000 dilution). Finally, 100 μl of horseradish peroxidase (HRP) chromogenic 3,3',5,5'-tetramethylbenzidine (TMB) substrate solution (Dako) were added. The reaction was stopped by the addition of 1 M sulfuric acid and recorded at 450 nm using a Tecan Infinite M200 plate reader.

Large Scale Protein Expression and Purification in Mammalian Cells pFUSE containing the DR3 variants was transfected to 500 ml of 293F cells in Freestyle media according to the manufacturer's procedure. Six days post transfection the media was collected and concentrated fivefold using a 10K Amicon ultrafiltration device, subsequently the concentrated supernatant was dilute six fold with 30 mM Tris pH 8.3 (buffer A). The final pH was measured to be 8.25 and the supernatant was loaded onto MonoQ column (GE). Next, the column was washed with 20 column volumes of buffer A and the protein was eluted by applying a gradient of 20 column volumes from buffer A to buffer B (30 mM Tris pH 8.3 and 0.5 M NaCl), fractions were collected during the whole elution process. Fraction activity was measured by ELISA, active fractions were pooled together dialyzed against PBS containing 1.5 mM DTT and then diluted tenfold into 50 mM NaCitrate 25 mM NaCl pH 5.8 (buffer C). The diluted active fractions were directly loaded on a SP column (GE), and the column was washed with buffer C till the OD 280 was stable. The SP column was eluted by applying a gradient from buffer C to a buffer containing 50 mM NaCitrate 450 mM NaCl pH 5.8 (buffer D) with a gradient length of 23 column volumes, fractions were collected during the whole elution process. Samples were run on a SDS PAGE gel and fractions that contained a major band of approximately 47 kDa corresponding to DR3-Fc fusion protein were pooled.

The pooled fractions were diluted two fold into 2 M $NH_3SO_4$ 50 mM Tris pH 7.3 and then loaded on a butyl HIC column (GE). The butyl column was washed for more than 20 column volumes with 1 M $NH_3SO_4$ 200 mM NaCl 25 mM NaCitrate pH 5.8 and was eluted by applying a 21 column volumes gradient to buffer containing 50 mM citrate 25 mM NaCl pH 5.8, elution fractions were collected and analyzed by SDS PAGE gel. Fractions containing the DR3-FC at a purity of 90% or higher were pooled together dialyzed against PBS containing 1.5 mM DTT and flushed freezed in liquid nitrogen in small aliquots for future use.

CD4+ Cell Based Assay for the Inhibition of TL1A-Induced IFN-γ Secretion

PBMC were isolated from blood of normal healthy volunteers using Lymphoprep™ (Axis shield, Oslo, Norway) according to the manufactures instructions, the PBL fraction was isolated subsequent to incubation of the PBMC in a flask at 37° C. for three hours and the non-adherent fraction was designated as PBL. The isolation of untouched CD4+ T cell subset was performed using CD4+ or T cell isolation kit (Miltenyi Biotec, Auburn, Calif.) as described by the manufacturer. PBL were incubated with IL-12 (2 ng/ml) and IL-18 (50 ng/ml) with or without TL1A (100 ng/ml) or DR3 variants at different concentrations for 72 h. The cultured media was collected and the levels of IFN-γ were quantitated through the use of ELISA kits (PeproTech) according to manufacturer description.

Affinity Measurements Using Surface Plasmon Resonance

The affinity of TL1A binding to DR3 variants was determined by surface plasmon resonance (SPR) measurements on a ProteOn XPR36 (Bio-Rad) instrument. All samples were in PBS containing 2 mM of DTT. A GLC Chip was air-initialized and activated with EDC/S-NHS. 5 μg from each of the DR3 variants were diluted in acetate buffer, pH 5.5, and immobilized onto the chip as a reference and BSA was also loaded onto the chip. After blocking available unbound sites on the chip with ethanolamine, the chip was washed with HBST buffer and rotated. TL1A was run at 30 μl/min for 300 sec at various concentrations (100, 50, 25, 12.5 and 6.25 nM), followed by a 10-min dissociation step.

Binding parameters were determined with the Langmuir single binding site model, using the Bio-Rad's proteOn Manager software V2.1.2.05.

Directed Evolution Methodologies

In the past few years, directed evolution methodologies have proven to be highly valuable for generating proteins with improved functions. Directed evolution methodologies are based on the principles of natural Darwinian evolution and consist of two major steps: (i) Creation of genetic diversity in the target gene in the form of gene-libraries and (ii) effective selection or screening of those libraries for the desired activity. Directed evolution has been employed for improving the catalytic activity of enzymes, for altering substrate specificity, for enhancing thermostability and for augmenting expression in recombinant systems. In addition, this approach was used to generate proteins with significantly enhanced affinity for various ligands.

Example 1

Generation of DR3-ECD Gene Libraries

The DR3 receptor is a transmembrane protein containing an N-terminal signal peptide, followed by a 171 amino acid (aa)-long ECD of which aa 35-141 are homologues to the tumor necrosis factor receptor 1, a transmembrane domain and a cytoplasmic tail containing a death domain (aa 343-419). The full length ECD of the receptor, consisting of 171 residues, was cloned as a first step in the generation of DR3 mutant library. Next, multiple sequence alignment of DR3 ECD were used to generate a focused back-to-consensus DR3 library (FIG. 2). In recent years, several approaches have been developed to generate small and functionally rich gene libraries based on the structure, function and evolution of the target protein. One of these approaches is by targeted mutagenesis of residues that deviate from the consensus sequence of the gene family to generate a back-to-consensus library. This library approach was shown to enhance the stability and activity of the target protein.

Figure 2B:
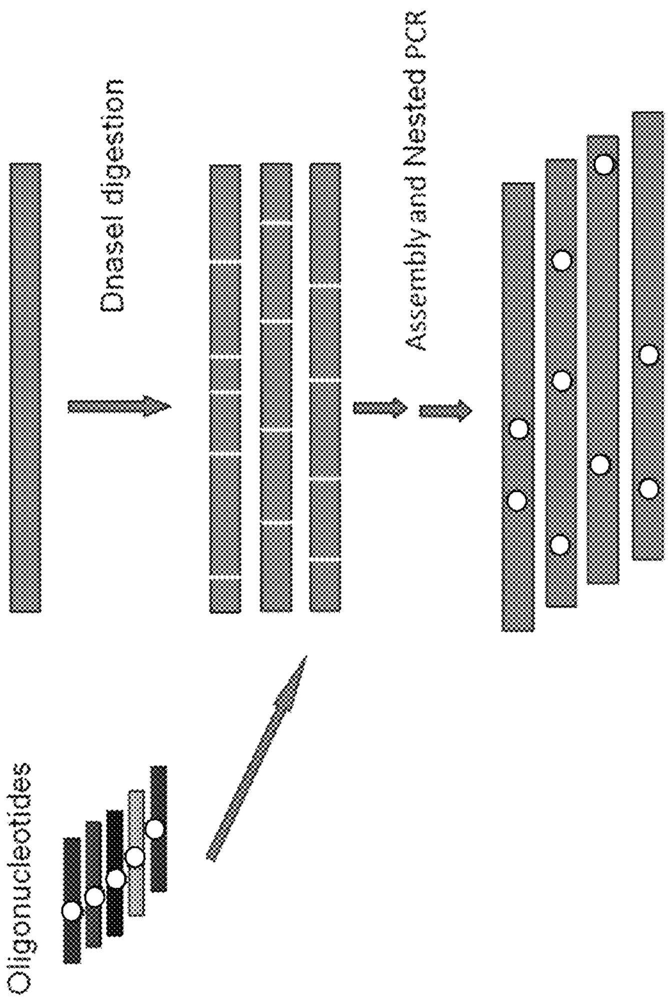

To identify target residues that deviate from the family consensus in the DR3 ECD, 12 mammalian DR3 sequences were aligned. We identified 13 different positions which deviate from the DR3 family consensus (Table 1). To generate a DR3 gene library containing back-to-consensus mutations, we adapted a recently developed methodology termed ISOR (Incorporation of Synthetic Nucleotide via Gene Reassembly) for partial mutagenesis of the targeted positions (Herman, A. & Tawfik, D. S. (2007). *Protein Eng Des Sel* 20, 219-26). This methodology is an adaptation of gene shuffling and allows simultaneous diversification of specific residues by spiking with synthetic oligonucleotides containing the desired mutations during the gene assembly process (FIG. 2B). Following library generation, sequencing of 6 random DR3 library variants indicated an insertion of 3-8 back-to-consensus mutations per gene with an average of ~4 mutations per gene. Each library variant carried a random and different subset of mutated residues (data not shown).

TABLE 1

Amino acid residue frequency in the DR3 protein.

| Position[a] | Human DR3 | DR3 family[b] | Mutation[c] |
|---|---|---|---|
| 4 (1) | R | P (8/12) | R4P |
| 15 (12) | H | Q (9/12) | H15Q |
| 18 (15) | I | Y (5/12) | I18Y |
| | | N (5/12) | I18N |
| 38 (35) | E | K (5/12) | E38K |
| 47 (44) | V | P (10/12) | V47P |
| 51 (48) | D | G (9/12) | D51G |
| 56 (53) | W | R (8/12) | W56R |
| 61 (58) | N | E (5/12) | N61G |
| | | K (3/12) | N61K |
| 65 (61) | A | T (7/12) | A65T |
| 93 (90) | K | E (3/12) | K93E |
| | | Q (3/12) | K93Q |
| 101 (98) | Q | S (6/12) | Q101S |
| 104 (101) | Q | P (6/12) | Q104P |
| 129 (126) | L | P (10/12) | L129P |

[a]Amino acid residue positions are shown according to the human DR3 protein sequence.
[b]Frequency of a given residue in homolog DR3 proteins based on the alignment of 12 homolog DR3 (ECD) proteins from different species.
[c]Amino acid mutations spiked into DR3 (ECD) to generate the 'back to consensus' library (see text and Materials and Methods for details)

Example 2

Enrichment of the DR3 Library Using Yeast Surface Display

Figure 3A:
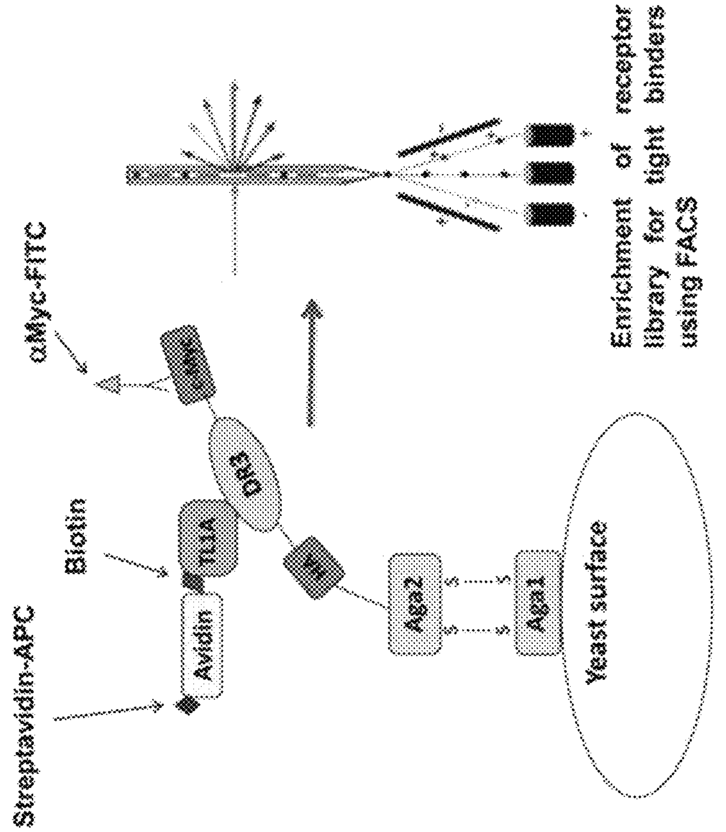
FIGS. 3A-B. Screening for improved DR3 mutants using yeast surface display (YSD). (A) YSD of DR3; DR3 is displayed as an Aga2 fusion on the surface of the yeast. Expression and TL1A binding are detected by fluorescent antibodies and streptavidin, respectively. (B) Flow cytometry histogram analysis of cell population displaying WT DR3, DR3 mutant library after two rounds (R2) and three rounds of enrichment (R3) for binding to TL1A. Cell population that lacks surface display is shown in black. Analysis of cells was performed following incubation with 0.2 μM of TL1A.
Figure 3B:
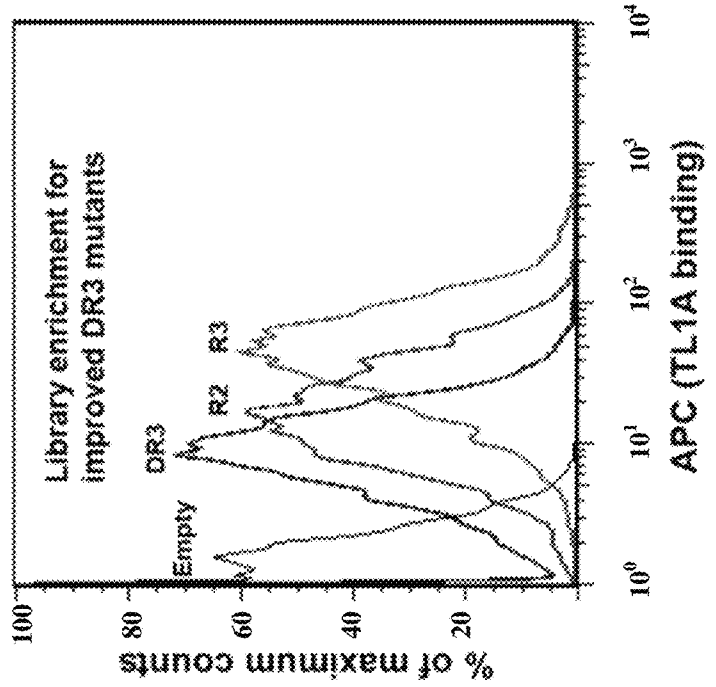

Yeast surface display (YSD) is a powerful method for engineering proteins with increased affinity, specificity and stability. The YSD approach provides several advantages over other methods for high-throughput screening of large mutant libraries. This approach enables quantitative screening of large libraries through the use of fluorescence-activated cell sorting, allowing the "real time" analysis of the library characteristics and fine tuning of the selection threshold. The YSD approach was utilized to display the DR3 on the yeast cell surface and to examine its binding to TL1A (FIG. 3). The display level of DR3 was monitored using fluorescein isothiocyanate (FITC)-labeled antibodies against the myc tag introduced at the C-terminal of the protein. Binding to TL1A was monitored using biotinylated α-DR3 antibodies followed by incubation with streptavidin conjugated to allophycocyanin (APC). To enrich the library for mutants with enhanced display levels and affinity to TL1A, yeast cells displaying the DR3 library were incubated with TL1A and more than $5*10^6$ cells were analyzed and sorted by fluorescence-activated cell sorting (FACS), based on a fluorescence expression and binding signal. Three iterative rounds of enrichment were performed leading to a continuous increase in the mean fluorescence of the population (FIG. 3B).

Example 3

Screening of the Enriched DR3 Library Using ELISA

Figure 4:
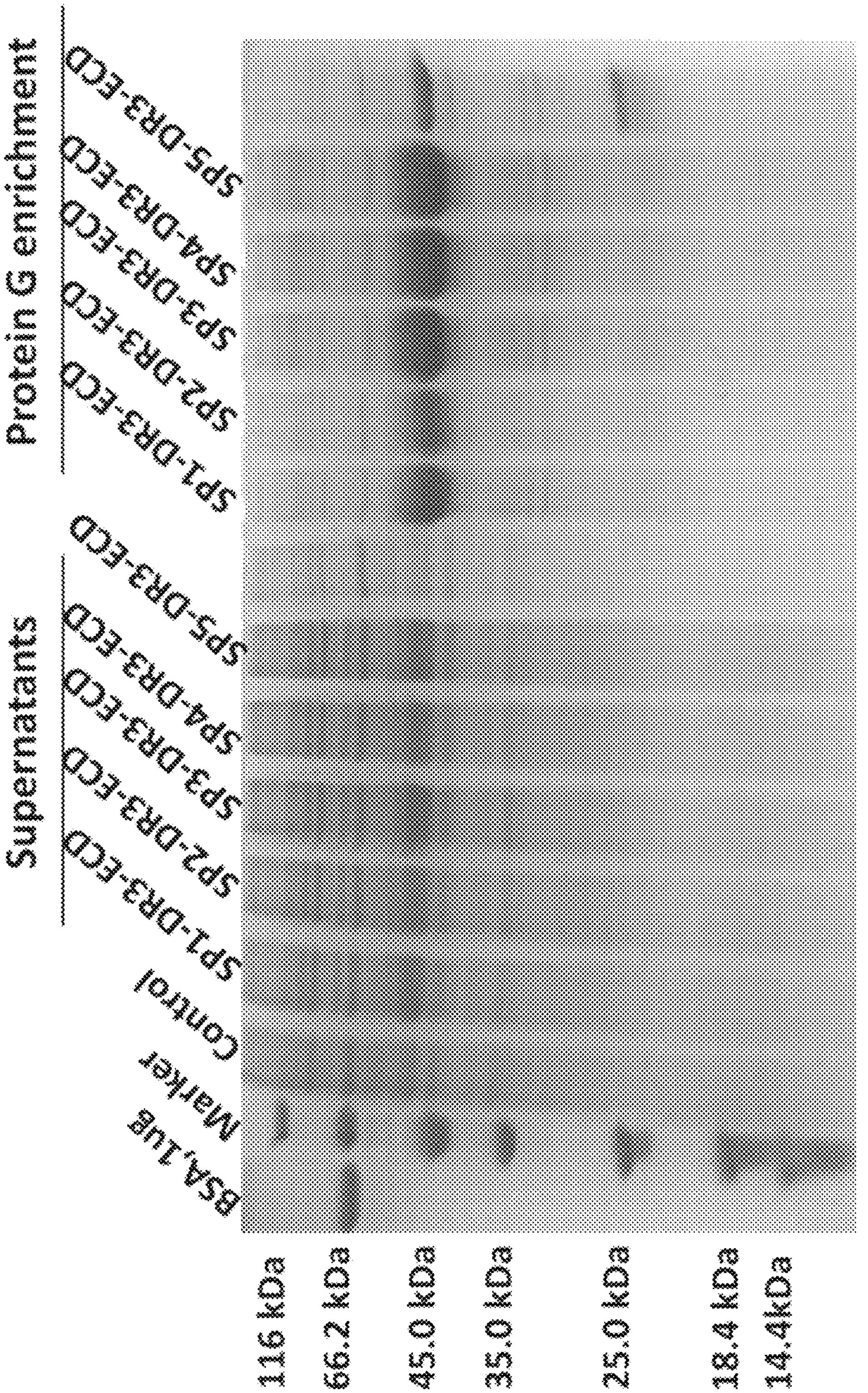
FIG. 4. Optimization of DR3 expression in HEK293T cells. The level of secreted DR3 containing different leader peptides (SP1-5) was analyzed using SDS PAGE before and after protein G enrichment. Most conditions shows high yield of DR3 expression.
Figure 5A:
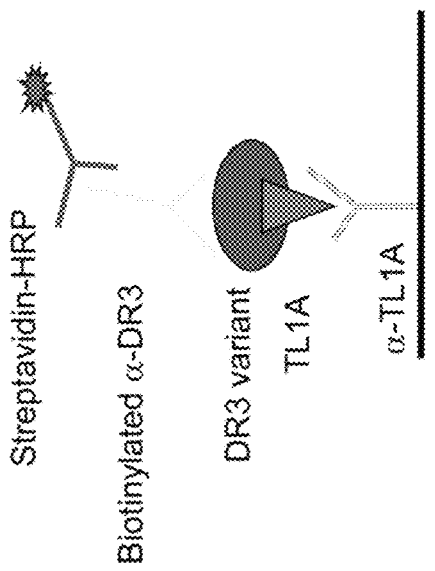
FIGS. 5A-B. ELISA experiments for the detection of DR3-TL1A interaction. (A) Schematics of the ELISA for DR3 binding TL1A. The ELISA plate is coated with anti-TL1A antibodies and subsequently, TL1A. Different DR3 variants are then added to the plate and binding to TL1A is detected using specific biotinylated anti-DR3 antibodies as the primary antibody and streptavidin-HRP. (B) DR3 calibration curve. Commercially available WT DR3 at five different concentrations was used in the TL1A-binding ELISA assay.
Figure 5B:
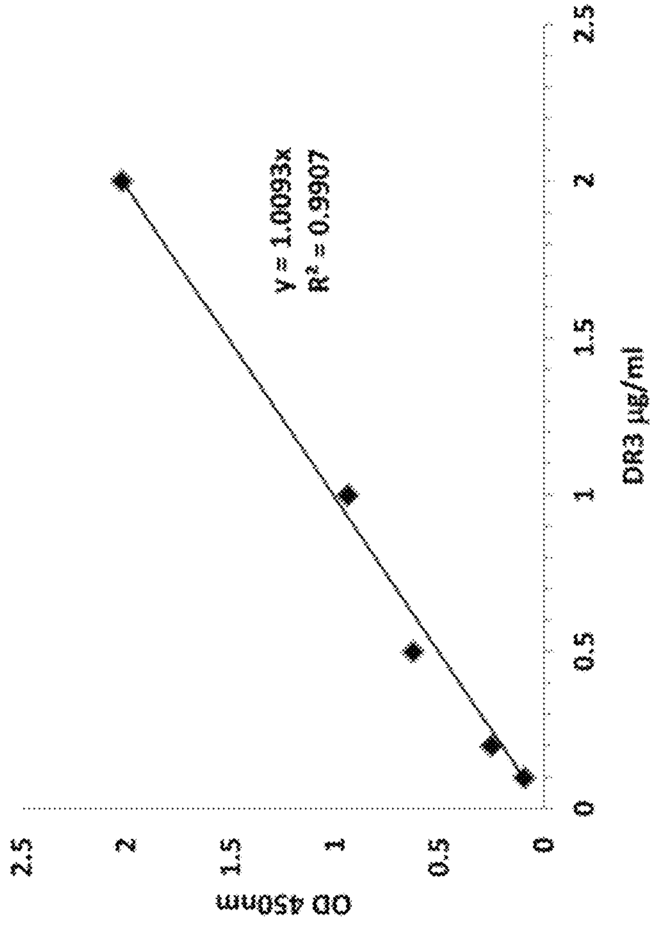
Figure 6:
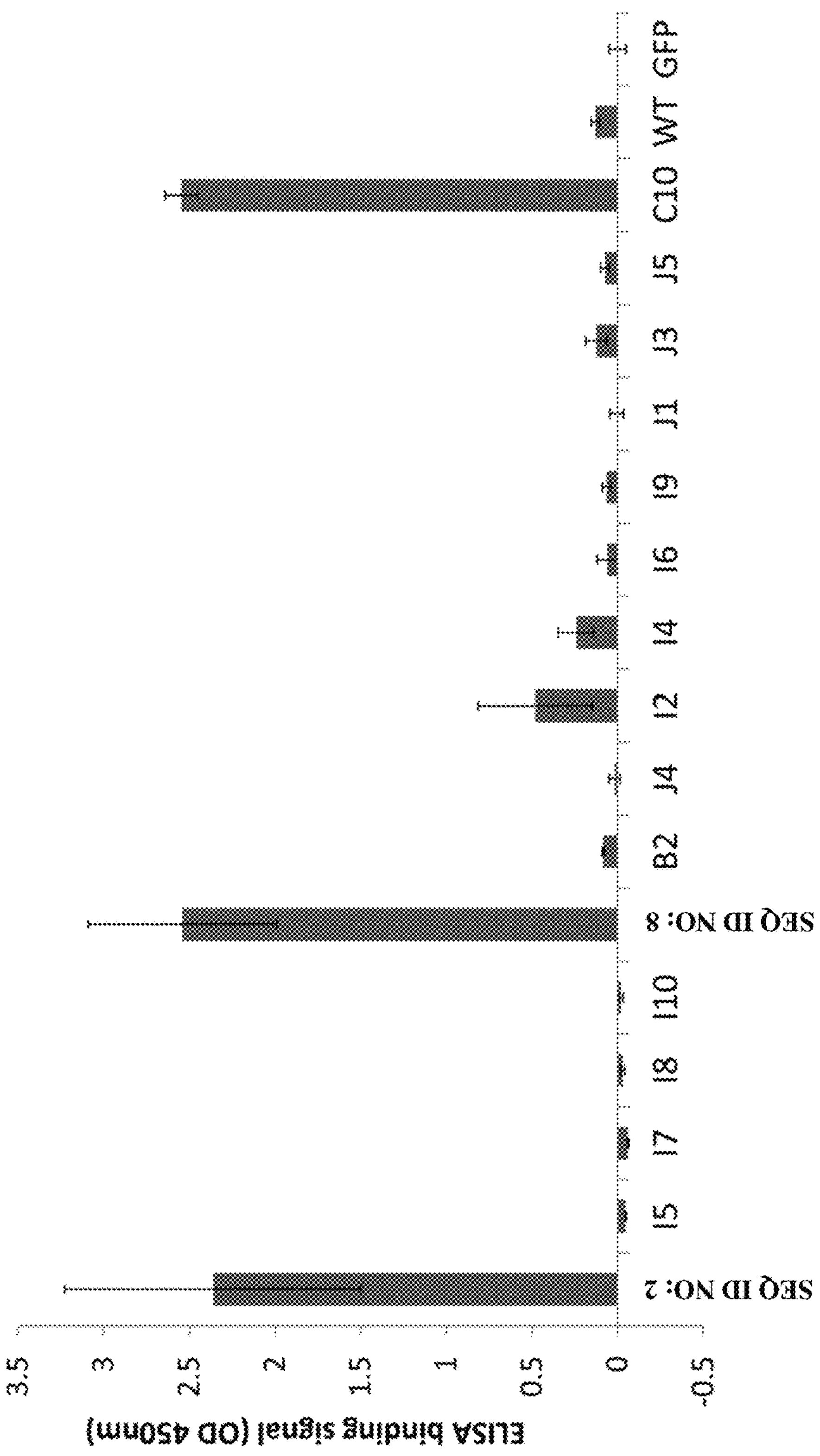
FIG. 6. Representative screening of DR3 mutants for the identification of candidate mutants with improved binding affinity or stability. The screening was performed following transfection and expression of DR3 mutants in HEK293T cells. Media containing the DR3 variants was directly applied to ELISA plates containing immobilized TL1A to detect the level of TL1A-DR3 interactions. Variants having amino acid sequences as set forth in SEQ ID NO: 5 and SEQ ID NO: 8 were expressed on a large scale and purified for subsequent analysis (Table 2) while mutant C10 contained a truncation and was discarded from further analysis.

To identify single DR3 mutant candidates with enhanced binding affinity for TL1A, the FACS-enriched library was sub-cloned into a mammalian vector containing leader peptide and fused with human IgG1 Fc. It was previously shown that the extracellular domain of many receptors is highly glycosylated and that such glycosylation can significantly contribute to receptor conformation and binding to the target ligand. Thus, the mammalian based expression of soluble DR3 receptor offers the advantage of maintaining the native protein posttranslational modifications including glycosylation. To obtain high level of DR3 expression in mammalian cells, the leader peptide sequence was optimized (FIG. 4), transfection and expression conditions in HEK293F cells (see Experimental Procedures for details). To facilitate the screening of a relatively large number of DR3 mutants, cells were transfected in 24 plate format and the secreted DR3 was examined for TL1A interaction using ELISA. A fast and sensitive ELISA that is based on immobilizing TL1A on multi-well plates and detecting DR3 binding using specific antibodies was developed (FIG. 5). To examine the dynamic range for detection of the DR3-TL1A interaction, the concentrations of the DR3 applied to the plate were varied and the assay was found to be highly sensitive enabling the detection of a large range of DR3 concentrations (FIG. 5B). Using this assay, ~250 DR3 mutants from the FACS-enriched library were expressed in HEK293F cells and screened for binding to TL1A. Overall, this screening effort allowed the isolation of 7 candidate mutants that exhibit increased binding relative to the WT DR3 during the screening experiments (FIG. 6).

Example 4

Characterization of Eight Selected DR3 Mutants

To characterize the seven selected DR3 mutants we sequenced, expressed and purified the proteins in mammalian cells (see Table 2 for the list of mutations). For mammalian expression and purification, HEK293F cells were transiently transfected and the media was collected after seven days. When attempting to purify the DR3 variants using protein A affinity chromatography, a significant loss of DR3 activity following the elution step from the protein A resin was found. This loss is due to the low pH of the elution buffer. Therefore an alternative purification protocol for the DR3 variants for obtaining highly pure DR3 proteins was developed. This purification protocol is based on ion exchange chromatography followed by hydrophobic column purification (see Experimental Procedures for details).

TABLE 2

List of mutations in selected DR3 variants

| # Variant | Mutations | | | | | | | # of mutations |
|---|---|---|---|---|---|---|---|---|
| SEQ ID NO: 7 | E38K | V47P | A65T | Q101S | | | | 4 |
| SEQ ID NO: 5 | E38K | V47P | W56R | A65T | K93A | Q101S | | 6 |
| SEQ ID NO: 6 | H15Q | V47P | W56R | Q104P | | | | 4 |
| SEQ ID NO: 8 | H15Q | E38K | V47P | D51G | N61E | Q101S | | 6 |
| SEQ ID NO: 3 | I18T | V47P | D51G | N61E | K93E | Q104P | L129P | 7 |
| SEQ ID NO: 2 | I18T | V47P | D51G | A65T | K93A | Q101S | L129P | 7 |
| SEQ ID NO: 4 | I18Y | D51G | K93E | L129P | | | | 4 |
| SEQ ID NO: 9 | H15Q | V47P | N61E | K93E | Q101S | Q104P | L129P | 7 |

Next, the TL1A binding affinity to the different DR3 variants was characterized using surface plasmon resonance (Table 3). The affinity of the WT DR3 to TL1A was 45 nM, a value that is in excellent agreement with the previously reported TL1A binding affinity. Interestingly, the DR3 variant having SEQ ID NO: 2 exhibited 5-fold increased TL1A binding affinity relative to WT DR3. DR3 variant having SEQ ID NO:3 exhibited 6.6-fold increased TL1A binding affinity relative to WT DR3, DR3 variant having SEQ ID NO:5 exhibited 1.7-fold increased TL1A binding affinity relative to WT DR3 and DR3 variant having SEQ ID NO:2 exhibited 4.6-fold increased TL1A binding affinity relative to WT DR3 (Table 3).

TABLE 3

Kinetic rate constants of TL1A cytokine binding to DR3-Fc variants as Determined by SPR

| Immobilized Ligand | $k_a$(1/Ms) | $K_d$ (1/s) | $K_d$ (M) | Fold increase in Affinity |
|---|---|---|---|---|
| WT | $1.60*10^4$ | $7.20*10^{-4}$ | $4.49*10^{-8}$ | — |
| SEQ ID NO: 2 | $4.26*10^4$ | $3.51*10^{-4}$ | $8.26*10^{-9}$ | 5 |
| SEQ ID NO: 5 | $2.39*10^4$ | $6.43*10^{-4}$ | $2.69*10^{-9}$ | 1.7 |
| SEQ ID NO: 3 | $3.49*10^4$ | $2.37*10^{-4}$ | $6.79*10^{-9}$ | 6.6 |
| SEQ ID NO: 4 | $3.63*10^4$ | $3.57*10^{-4}$ | $9.83*10^{-9}$ | 4.6 |

Figure 7A:
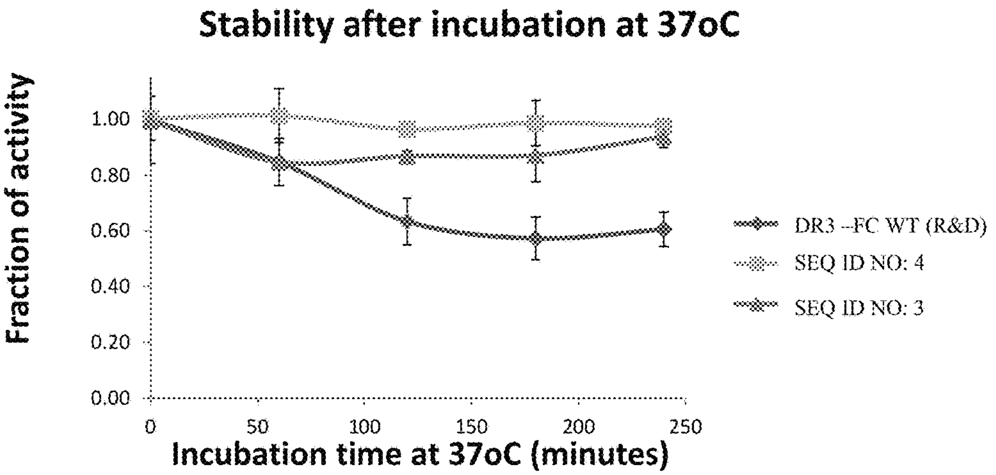
FIGS. 7A-D. The effect of temperature on the variants activity. (A) Binding activity incubation at 37° C. 3 ug/ml of the DR3 mutants having the amino acid sequence of SEQ ID NO: 3 and SEQ ID NO: 4 dissolved in PBS, 2 mM DTT were incubated for the indicated time at 37° C. and centrifuged at maximum speed for 5 minutes. Then 100 ul of the supernatant was used for an ELISA assay as described in materials and methods. The binding of the variants incubated at 37° C. at the indicated time is plotted as a fraction of binding of each variant that was incubated at T=0. (B) 3 ug/ml of the DR3 W.T and mutants having the amino acid sequence of SEQ ID NO: 2 and SEQ ID NO: 5 were incubated for 15 minutes at the indicated temperatures and centrifuged at maximum speed for 5 minutes. Subsequently, 100 ul of the supernatant was used for an ELISA assay as described above. The binding of the variants incubated at the indicated temperatures is plotted as a fraction of binding of each variant that was incubated at T=0. (C) Binding activity incubation at 25° C. 3 ug/ml of the DR3 mutants having the amino acid sequence of SEQ ID NO: 2 and SEQ ID NO: 5 were dissolved in PBS, 1 mM DTT were incubated for the indicated time at 25° C. and then centrifuged at maximum speed for 5 minutes. Subsequently 100 ul of the supernatant was used for an ELISA assay as described above. The binding of the variants incubated at 25° C. at the indicated time is plotted as a fraction of binding of each variant that was incubated at T=0. (D) Binding activity after 35 minutes incubation at 4° C., 37° C., 47° C. 3 ug/ml of the DR3 and the mutant having the amino acid sequence of SEQ ID NO: 4 were dissolved in PBS 1 mM DTT were incubated for ~35 min at the indicated temperature and centrifuged at maximum speed for 5 minutes. Then 100 ul of the supernatant was used for an ELISA assay as described above. The binding of the variants incubated at 37° C. and 47° C. was calculated as a fraction of binding of each variant that was incubated at 4° C.
Figure 7B:
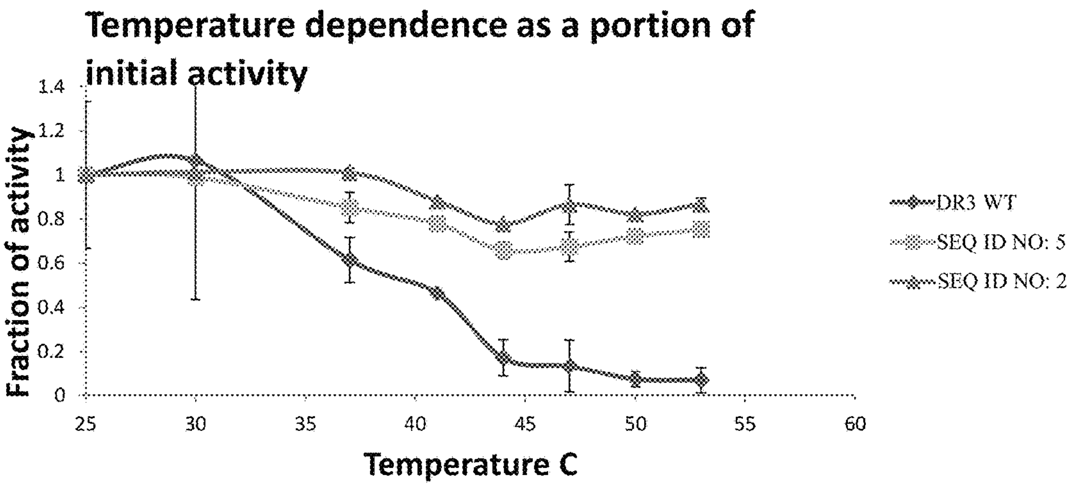
Figure 7C:
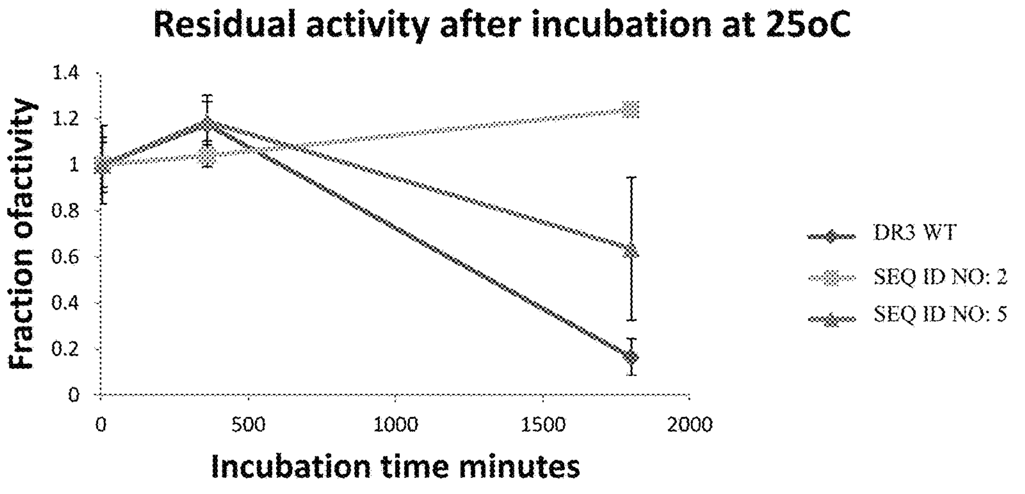
Figure 7D:
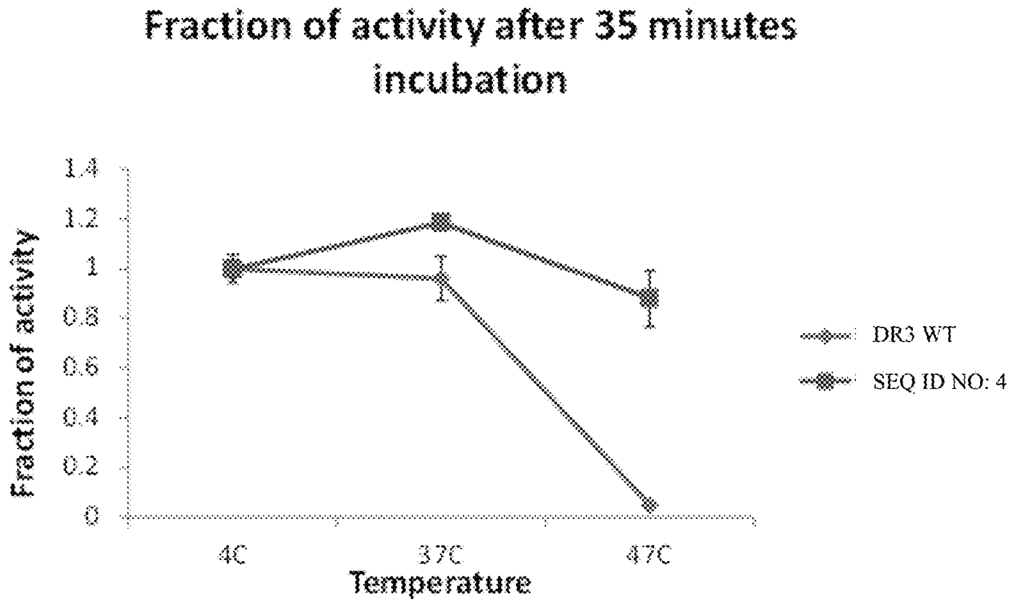
Figure 8:
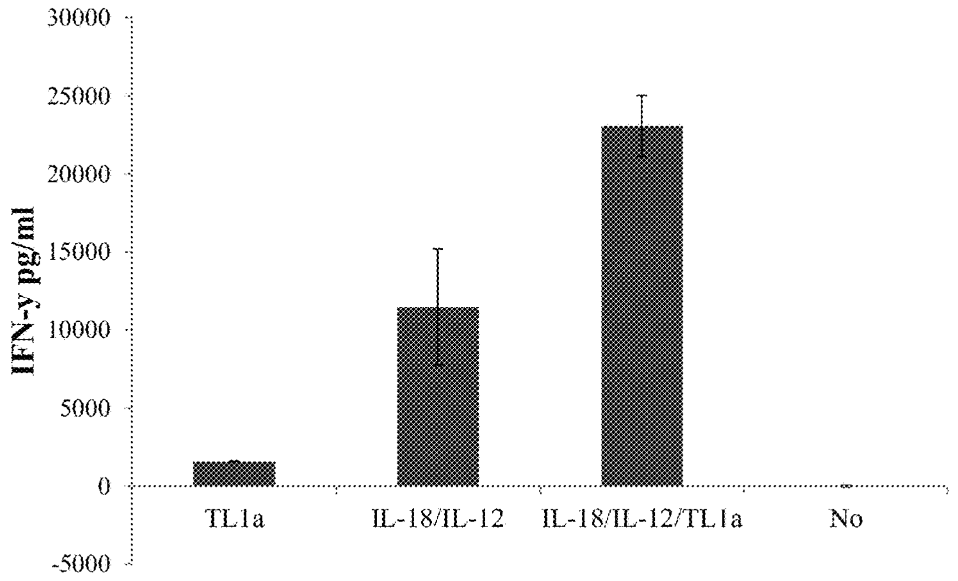
FIG. 8. TL1a enhances the IL-12/IL-18 dependent secretion of IFN-γ from CD4 cells. Human $CD4^+$ cells were incubated for 24 hours with 100 ng/ml TL1A, 2 ng/ml IL-12 and 50 ng/ml IL-18. The 1:10 diluted cell supernatant was analyzed by ELISA for detection of IFN-γ.

Next, the ability of the selected DR3 variants to bind to TL1A under different temperatures, relative to the DR3 WT protein, was tested. First, DR3 variants comprising SEQ ID NO: 3 and SEQ ID NO: 4 were found to exhibit higher binding activity following prolonged incubation at 37° C. compared to DR3 WT (FIG. 7A). Next, the ability of DR3 variants comprising SEQ ID NO: 2 and SEQ ID NO: 5 to bind to TL1A was found to be stable, under different temperatures while DR3 WT ability to bind to TL1A was decreased (FIG. 7B). In addition, following incubation at 25° C. the ability of DR3 WT to bind to TL1A was decreased faster compared to DR3 variants comprising SEQ ID NO: 2 and SEQ ID NO: 5 (FIG. 7C). The binding activity of DR3 WT was substantially decreased following 35 minutes incubation at 47° C., while DR3 variant comprising SEQ ID NO: 4 showed stable binding activity (FIG. 7D). To examine the ability of the engineered DR3 mutants to inhibit TL1A binding to the endogenous DR3 receptor in cells, we established a cell-based assay. The assay is based on measuring IFN-γ secretion following TL1A addition in conjunction with IL-12 and IL-18 to human CD4+ cells. Previously, it was shown that TL1A cooperate with IL-12 and IL-18 to induce IFN-γ in T cells and that the extant of IFN-γ secretion is higher in CD4+ cells. Furthermore, TL1A was demonstrated to enhance the IL-12/IL-18 dependent secretion of IFN-γ in CD4+ cells (FIG. 8).

Figure 9A:
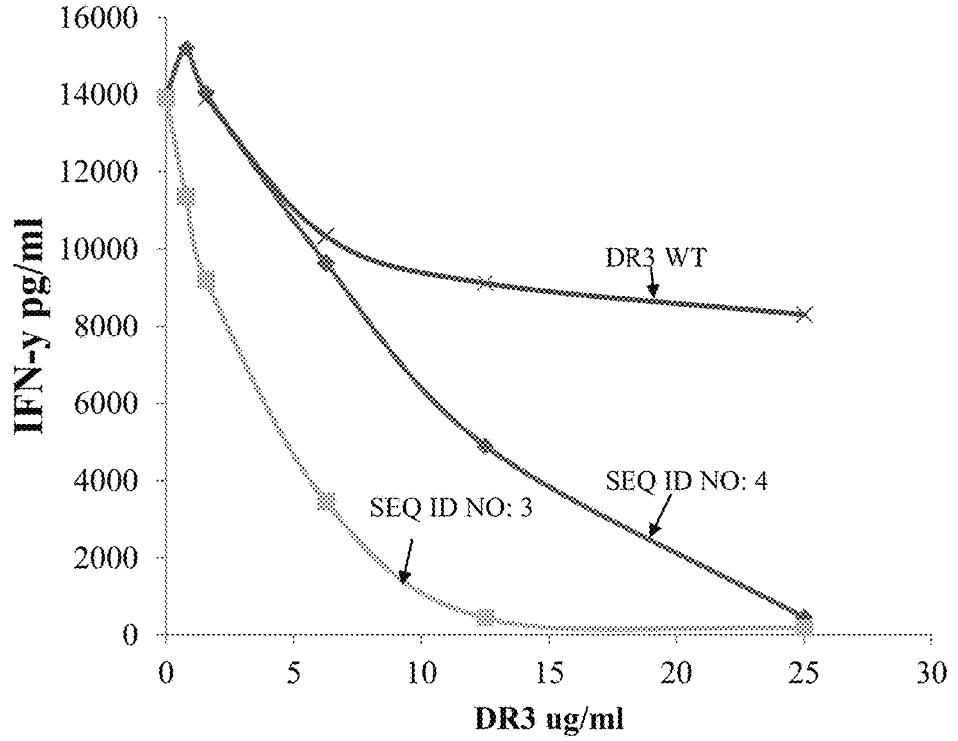
FIGS. 9A-B. The effect of the variants of the invention on TL1A-induced secretion of IFN-γ in human CD4+. $CD4^+$ cells were incubated for 24 hours with 100 ng/ml TL1A, 2 ng/ml IL-12 and 50 ng/ml IL-18 and different concentrations of (A) soluble DR3 WT (rectangles), variants having the amino acid sequence of SEQ ID NO: 4 (triangles) and SEQ ID NO: 3 (circles) variants; or (B) variant having the amino acid sequence of SEQ ID NO:2. The 1:10 diluted cell supernatant was analyzed by ELISA for detection of IFN. The data represent the average of two independent repeats of each experiment.
Figure 9B:
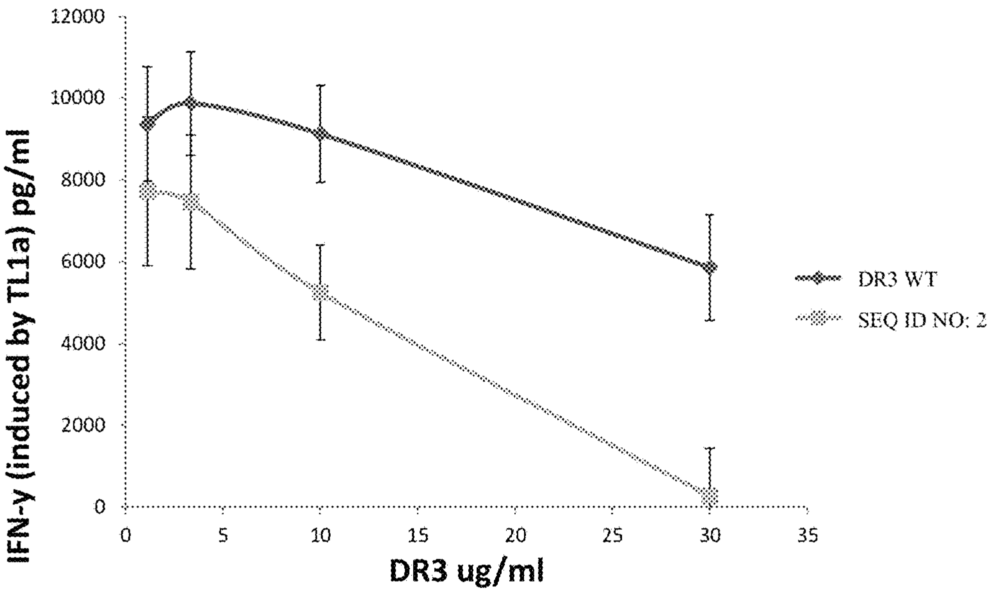

The addition of soluble DR3 together with TL1A prevents ligand binding to the endogenous DR3 receptor due to competition, thus leading to reduced IFN-γ secretion. We found that addition of high concentrations of DR3 to the CD4+ T cells together with 100 ng/ml of TL1A is sufficient to inhibit TL1A-induced IFN-γ secretion. The effect of the variants of the invention on TL1A-induced secretion of IFN-γ in human CD4+ was examined. A significant decrease of TL1A-induced secretion of IFN-γ in the presence of DR3 variants comprising SEQ ID NO: 3 and SEQ ID NO: 4. Furthermore, high concentration of DR3 variants was demonstrated to inhibit the secretion of IFN-γ (FIG. 9A, B).

While the present invention has been particularly described, persons skilled in the art will appreciate that many variations and modifications can be made. Therefore, the invention is not to be construed as restricted to the particularly described embodiments, and the scope and concept of the invention will be more readily understood by reference to the claims, which follow.

Example 5

In Vivo Trials

Intraperitoneal Cavity TL1a and DR3 Injection

DR3 WT and variants comprising SEQ ID NO: 2, SEQ ID NO: 3, SEQ ID NO: 4 or PBS at various concentrations ranging from 0.5 to 20 mg/kg are injected into the intraperitoneal cavity, following 30 minutes from injection, 0.2 mg/kg human TL1A or PBS are injected into the intraperitoneal cavity of model animal (e.g., C57BL/6 or Balb/c mice), six hours subsequent to the human TL1A injection the intraperitoneal cavity is washed with 1 ml PBS and analyzed for the level of IL-13 and IL-5 by ELISA. This assay can be performed as described in Yu X et al., 2014, Mucosal Immunol; 7(3):730-40, the contents of which are hereby incorporated by reference in their entirety.

In another experiment 0.2 mg/kg human TL1A and a range of 20 mg/kg-0.5 mg/kg DR3 WT or DR3 variants comprising SEQ ID NO: 2, SEQ ID NO: 3 and SEQ ID NO: 4 or PBS are mixed together and the mixture is injected into the intraperitoneal cavity of model animal, six hours subsequent to the initial injection the intraperitoneal cavity is washed with PBS and analyzed for the level of IL-13 and IL-5 by ELISA.

Adoptive Transfer Model

Stem cells that over express the human gene of TL1A under inducible conditions by lentiviral transfection are produced. In one example, this assay can be performed by using inducible systems as described in Pan H et al., 2008, J Immunol Methods. 329(1-2):31-44 the contents of which are hereby incorporated by reference in their entirety. One skilled in the art will appreciate that other inducible systems known in the art can be used. For example, 500,000 cells of CD45RDhi/humanTL1A or CD45RDhi are injected into the intraperitoneal cavity of Rag1−/− mice and disease severity is monitored for eight weeks before subjecting the sacrificed mice to histological analysis.

Analysis of the experiment utilizes a scoring system regarding changes the effect of the cells. The scoring system includes scores from 0 to 4 representing abnormalities regarding change in body weight: (0, no weight loss; 1, 1% to 5% weight loss; 2, 5% to 10% weight loss; 3, 10% to 15% weight loss; 4, more than 15% weight loss), stool consistency (0, firm dry stool; 1, moist stool; 2, soft adherent stool; 3, large soft pliable stool; 4, liquid stool), fecal occult blood test using Hemoccult II SENSA (Beckman Coulter, Brea, Calif.; 0, no color; 1, flecks of blue; 2, up to 50% blue; 3, more than 50% blue; 4, gross red blood), these three criteria will be summed to a final score. Additionally gross inflammation of the colon and small intestine as well as quantitative histology score of the duodenum, jejunum and ileum will be performed: A) inflammation: 0, normal; 1, mild; 2, moderate; 3, severe; B) Crypt damage: 0, none; 1, basal one-third damaged; 2, basal two-third damaged; 3, more than two-third damages; C) Villus change: 0, normal; 1, distortion; 2, branching; 3, atrophy and blunting.

In the second stage, mice injected with 500,000 cells of CD45RDhi/hTL1a are further injected with PBS, DR3 WT or variants disclosed herein (e.g., SEQ ID NO: 2, SEQ ID NO: 3 or SEQ ID NO: 4) in a range of 0.5 mg/kg-20 mg/kg into the intra peritoneum cavity twice a week. The mice are scored for disease severity and histology score is assigned as disclosed above.

Dextran Sulfate Sodium (DSS) Induced Colitis in Transgenic Mice

Transgenic mice strain that overexpressing the human gene of TL1A (hTL1a) under the promoter of CD11c or any other suitable promoter are produced. The transgenic mice are administered with 3% DSS (w/v) water on days 1 to 5, 8 to 12, 15 to 19, and 22 to 26 of the experiment in a similar fashion to Takedastu et al 2008, Gastroenterology, 135(2): 552-567. Alternatively, in cases when transgenic mice do not tolerate 3% DSS a dose of 2% or 1.5% of DSS are added to the drinking water.

Analysis of the experiment results utilizes a scoring system from 0 to 4 abnormalities regarding change in body weight: weight (0, no weight loss; 1, 1% to 5% weight loss; 2, 5% to 10% weight loss; 3, 10% to 15% weight loss; 4, more than 15% weight loss), stool consistency (0, firm dry stool; 1, moist stool; 2, soft adherent stool; 3, large soft pliable stool; 4, liquid stool), fecal occult blood test using Hemoccult II SENSA (Beckman Coulter, Brea, Calif.; 0, no color; 1, flecks of blue; 2, up to 50% blue; 3, more than 50% blue; 4, gross red blood), these three criteria are summed to a final score. Additionally gross inflammation of the colon and small intestine Macroscopic evidence normal gut morphology will be signed a score of 0; mild bowel wall thickening without hyperemia is assigned a score of 1; moderate bowel wall thickening with hyperemia a score of 2; severe bowel wall thickening with rigidity and hyperemia a score of 3; and severe bowel wall thickening with rigidity, hyperemia, and adhesions is assigned a score of 4. A quantitative histology score of the duodenum, jejunum and ileum is performed: A) inflammation: 0, normal; 1, mild; 2, moderate; 3, severe; B) Crypt damage: 0, none; 1, basal one-third damaged; 2, basal two-third damaged; 3, more than two-third damaged; C) Villus change: 0, normal; 1, distortion; 2, branching; 3, atrophy and blunting."

These transgenic human TL1A mice are administered twice a week by intraperitoneal injection of PBS, DR3 WT or DR3 variants (e.g., SEQ ID NO: 2, SEQ ID NO: 3 or SEQ ID NO: 4) at various concentrations ranging from 0.5 to 20 mg/kg twice a week. The mice are scored for disease severity for 26 days, before they are sacrificed and gross inflammation and histology score are assigned.

Chronic Dextran Sulfate Sodium (DSS) Model

Model animals (e.g., C57BL/6 mice) are administered with 3% DSS (w/v) water on days 1 to 5, 8 to 12, 15 to 19, and 22 to 26 of the experiment in a similar fashion to Takedatsu et al., 2008, Gastroenterology, 135(2): 552-567.

A scoring system from 0 to 4 abnormalities regarding change in body weight: weight (0, no weight loss; 1, 1% to 5% weight loss; 2, 5% to 10% weight loss; 3, 10% to 15% weight loss; 4, more than 15% weight loss), stool consistency (0, firm dry stool; 1, moist stool; 2, soft adherent stool; 3, large soft pliable stool; 4, liquid stool), fecal occult blood test using Hemoccult II SENSA (Beckman Coulter, Brea, Calif.; 0, no color; 1, flecks of blue; 2, up to 50% blue; 3, more than 50% blue; 4, gross red blood), these three criteria are summed to a final score. Additionally gross inflammation of the colon and small intestine Macroscopic evidence normal gut morphology will be signed a score of 0; mild bowel wall thickening without hyperemia is assigned a score of 1; moderate bowel wall thickening with hyperemia a score of 2; severe bowel wall thickening with rigidity and hyperemia a score of 3; and severe bowel wall thickening with rigidity, hyperemia, and adhesions will be assigned a score of 4. A quantitative histology score of the duodenum, jejunum and ileum will be performed: A) inflammation: 0, normal; 1, mild; 2, moderate; 3, severe; B) Crypt damage: 0, none; 1, basal one-third damaged; 2, basal two-third damaged; 3, more than two-third damaged; C) Villus change: 0, normal; 1, distortion; 2, branching; 3, atrophy and blunting.

DSS induced mice are administered twice a week with intraperitoneal injection of PBS, DR3 WT or variants having SEQ ID NO: 2, SEQ ID NO: 3 or SEQ ID NO: 4 at various concentrations ranging from 0.5 to 20 mg/kg twice a week. The mice are scored for disease severity for 26 days. Thereafter, the mice are sacrificed and gross inflammation and histology score is assigned.

Acute Model of Colitis: 2,4,6 trinitrobenze-nesulfonic Acid (TNBS)

Laboratory mice (e.g., C57BL/10) are induced by intrarectal administration of TNBS in 50% ethanol or just 50% ethanol as described in Scheiffele F et al., 2002, Curr Protoc Immunol. 2002, Chapter 15:Unit 15.19. The mice are induced with acute TNBS-colitis combined with intraperitoneal (IP) injection of the DR3-Fc variants at day −1 and 0, as previously described in Meylan, F et al., 2011, Mucosal Immunol; 4(2):172-85.

In order to assess receptor efficacy in inhibiting TNBS-induced colitis, DR3 WT, DR3 variants and mouse IgG (control) are injected in different concentrations (e.g., 2.5, 5, 10 and 20 mg/kg) into the intraperitoneal cavity of laboratory mice (e.g., C57BL/10 mice). To measure the level of protection against weight loss and mortality of the treated mice relative to the untreated mice, mice are weighed every day for five days, and a scoring system from 0 to 4 will be assigned to abnormalities regarding change in body weight: weight (0, no weight loss; 1, 1% to 5% weight loss; 2, 5% to 10% weight loss; 3, 10% to 15% weight loss; 4, more than 15% weight loss), stool consistency (0, firm dry stool; 1, moist stool; 2, soft adherent stool; 3, large soft pliable stool; 4, liquid stool). After five days mice are euthanized, and their colons are harvested for histological analysis. The colon samples isolated from these mice are sectioned and stained with hematoxylin and eosin (H&E) to identify areas of severe inflammation. Each section is scored in a blind fashion according to the severity of inflammation.

What is claimed is:

1. An amino acid molecule, comprising the amino acid sequence of GGTRSPRCDCAGDFHKKIGLFCCRGCPAGHYLKAPCTEPCGNSTCLVCPQDTFLAWE NHHNSECARCQACDEQASQVALENCSAVADTRCGCKPGWFVECQVSQCVSSSPFYCQ PCLDCGALHRHTRLLCSRRDTDCGTCLPGFYEHGDGCVSCPTSTLGSCPERCAAVCGW RQMF set forth in SEQ ID NO: 2.

2. The amino acid molecule of claim 1, having an increased binding affinity to human TNF-like 1A (TL1A), compared to SEQ ID NO: 13.

3. The amino acid molecule of claim 1, further comprising a peptide of the Fragment crystallizable (Fc) region of an antibody, optionally wherein said peptide of the Fragment crystallizable (Fc) region of an antibody comprises the amino acid sequence of VECPPCPAPPVAGPSVFLFPPK-PKDTLMISRTPEVTCVVVDVSHEDPEVKFN-WYVDGV EVHNAKTKPREEQYNSTYRVVSVLTVL-HQDWLNGKEYKCKVSNKGLPSSIEKTISKAK GQPREPQVYTLPPSREEMTKNQVSLTCLVKGFYPS-DIAVEWESNGQPENNYKTTPPVL DSDGSFFLYSKLT-VDKSRWQQGNVFSCSVMHEGLHNHYTQK-SLSLSPGK set forth in SEQ ID NO: 10.

4. The amino acid molecule of claim 3, further comprising a linker comprising the amino acid sequence of IEGRMDRS set forth in SEQ ID NO: 11, wherein said linker is fused to the carboxy terminus of said amino acid of SEQ ID NO: 2 and to the amino terminus of said peptide of the Fc region of an antibody.

5. A composition comprising the amino acid molecule of claim 1 and a carrier.

6. A polynucleotide molecule comprising a coding portion encoding the amino acid molecule of claim 4.

7. An expression vector comprising the polynucleotide of claim 6.

8. An isolated cell comprising the expression vector of claim 7.

9. A composition comprising the expression vector of claim 7 and a carrier.

10. A method of inhibiting TL1A-induced secretion of IFN-γ in a subject in need thereof, comprising the step of administering to said subject an effective amount of the composition of claim 5.

* * * * *

SEQUENCE LISTING

```
<160> NUMBER OF SEQ ID NOS: 25

<210> SEQ ID NO 1
<211> LENGTH: 176
<212> TYPE: PRT
<213> ORGANISM: Artificial sequence
<220> FEATURE:
<223> OTHER INFORMATION: syntetic polypetide
<220> FEATURE:
<221> NAME/KEY: MISC_FEATURE
<222> LOCATION: (15)..(15)
<223> OTHER INFORMATION: X is His or Gln
<220> FEATURE:
<221> NAME/KEY: MISC_FEATURE
<222> LOCATION: (18)..(18)
<223> OTHER INFORMATION: X is Ile, Thr or Tyr
<220> FEATURE:
<221> NAME/KEY: MISC_FEATURE
<222> LOCATION: (38)..(38)
<223> OTHER INFORMATION: X is Glu or Lys
<220> FEATURE:
<221> NAME/KEY: MISC_FEATURE
<222> LOCATION: (47)..(47)
<223> OTHER INFORMATION: X is Val or Pro
<220> FEATURE:
<221> NAME/KEY: MISC_FEATURE
<222> LOCATION: (51)..(51)
<223> OTHER INFORMATION: X is Asp or Gly
<220> FEATURE:
<221> NAME/KEY: MISC_FEATURE
<222> LOCATION: (56)..(56)
<223> OTHER INFORMATION: X is Trp or Arg
<220> FEATURE:
<221> NAME/KEY: MISC_FEATURE
<222> LOCATION: (61)..(61)
<223> OTHER INFORMATION: X is Asn or Glu
<220> FEATURE:
<221> NAME/KEY: MISC_FEATURE
<222> LOCATION: (65)..(65)
<223> OTHER INFORMATION: X is Ala or Thr
<220> FEATURE:
<221> NAME/KEY: MISC_FEATURE
<222> LOCATION: (93)..(93)
<223> OTHER INFORMATION: X is Lys, Glu or Ala
<220> FEATURE:
<221> NAME/KEY: MISC_FEATURE
<222> LOCATION: (101)..(101)
```

```
<223> OTHER INFORMATION: X is Gln or Ser
<220> FEATURE:
<221> NAME/KEY: MISC_FEATURE
<222> LOCATION: (104)..(104)
<223> OTHER INFORMATION: X is Gln or Pro
<220> FEATURE:
<221> NAME/KEY: MISC_FEATURE
<222> LOCATION: (129)..(129)
<223> OTHER INFORMATION: X is Leu or Pro

<400> SEQUENCE: 1

Gly Gly Thr Arg Ser Pro Arg Cys Asp Cys Ala Gly Asp Phe Xaa Lys
1               5                   10                  15

Lys Xaa Gly Leu Phe Cys Cys Arg Gly Cys Pro Ala Gly His Tyr Leu
            20                  25                  30

Lys Ala Pro Cys Thr Xaa Pro Cys Gly Asn Ser Thr Cys Leu Xaa Cys
        35                  40                  45

Pro Gln Xaa Thr Phe Leu Ala Xaa Glu Asn His His Xaa Ser Glu Cys
    50                  55                  60

Xaa Arg Cys Gln Ala Cys Asp Glu Gln Ala Ser Gln Val Ala Leu Glu
65                  70                  75                  80

Asn Cys Ser Ala Val Ala Asp Thr Arg Cys Gly Cys Xaa Pro Gly Trp
                85                  90                  95

Phe Val Glu Cys Xaa Val Ser Xaa Cys Val Ser Ser Ser Pro Phe Tyr
            100                 105                 110

Cys Gln Pro Cys Leu Asp Cys Gly Ala Leu His Arg His Thr Arg Leu
        115                 120                 125

Xaa Cys Ser Arg Arg Asp Thr Asp Cys Gly Thr Cys Leu Pro Gly Phe
    130                 135                 140

Tyr Glu His Gly Asp Gly Cys Val Ser Cys Pro Thr Ser Thr Leu Gly
145                 150                 155                 160

Ser Cys Pro Glu Arg Cys Ala Ala Val Cys Gly Trp Arg Gln Met Phe
                165                 170                 175


<210> SEQ ID NO 2
<211> LENGTH: 176
<212> TYPE: PRT
<213> ORGANISM: Artificial sequence
<220> FEATURE:
<223> OTHER INFORMATION: syntetic polypetide

<400> SEQUENCE: 2

Gly Gly Thr Arg Ser Pro Arg Cys Asp Cys Ala Gly Asp Phe His Lys
1               5                   10                  15

Lys Thr Gly Leu Phe Cys Cys Arg Gly Cys Pro Ala Gly His Tyr Leu
            20                  25                  30

Lys Ala Pro Cys Thr Glu Pro Cys Gly Asn Ser Thr Cys Leu Pro Cys
        35                  40                  45

Pro Gln Gly Thr Phe Leu Ala Trp Glu Asn His His Asn Ser Glu Cys
    50                  55                  60

Thr Arg Cys Gln Ala Cys Asp Glu Gln Ala Ser Gln Val Ala Leu Glu
65                  70                  75                  80

Asn Cys Ser Ala Val Ala Asp Thr Arg Cys Gly Cys Ala Pro Gly Trp
                85                  90                  95

Phe Val Glu Cys Ser Val Ser Gln Cys Val Ser Ser Ser Pro Phe Tyr
            100                 105                 110

Cys Gln Pro Cys Leu Asp Cys Gly Ala Leu His Arg His Thr Arg Leu
        115                 120                 125
```

-continued

```
Pro Cys Ser Arg Arg Asp Thr Asp Cys Gly Thr Cys Leu Pro Gly Phe
    130                 135                 140

Tyr Glu His Gly Asp Gly Cys Val Ser Cys Pro Thr Ser Thr Leu Gly
145                 150                 155                 160

Ser Cys Pro Glu Arg Cys Ala Ala Val Cys Gly Trp Arg Gln Met Phe
                165                 170                 175


<210> SEQ ID NO 3
<211> LENGTH: 176
<212> TYPE: PRT
<213> ORGANISM: Artificial sequence
<220> FEATURE:
<223> OTHER INFORMATION: syntetic polypeptide

<400> SEQUENCE: 3

Gly Gly Thr Arg Ser Pro Arg Cys Asp Cys Ala Gly Asp Phe His Lys
1               5                   10                  15

Lys Thr Gly Leu Phe Cys Cys Arg Gly Cys Pro Ala Gly His Tyr Leu
            20                  25                  30

Lys Ala Pro Cys Thr Glu Pro Cys Gly Asn Ser Thr Cys Leu Pro Cys
        35                  40                  45

Pro Gln Gly Thr Phe Leu Ala Trp Glu Asn His His Glu Ser Glu Cys
    50                  55                  60

Ala Arg Cys Gln Ala Cys Asp Glu Gln Ala Ser Gln Val Ala Leu Glu
65                  70                  75                  80

Asn Cys Ser Ala Val Ala Asp Thr Arg Cys Gly Cys Glu Pro Gly Trp
                85                  90                  95

Phe Val Glu Cys Gln Val Ser Pro Cys Val Ser Ser Ser Pro Phe Tyr
            100                 105                 110

Cys Gln Pro Cys Leu Asp Cys Gly Ala Leu His Arg His Thr Arg Leu
        115                 120                 125

Pro Cys Ser Arg Arg Asp Thr Asp Cys Gly Thr Cys Leu Pro Gly Phe
    130                 135                 140

Tyr Glu His Gly Asp Gly Cys Val Ser Cys Pro Thr Ser Thr Leu Gly
145                 150                 155                 160

Ser Cys Pro Glu Arg Cys Ala Ala Val Cys Gly Trp Arg Gln Met Phe
                165                 170                 175


<210> SEQ ID NO 4
<211> LENGTH: 176
<212> TYPE: PRT
<213> ORGANISM: Artificial sequence
<220> FEATURE:
<223> OTHER INFORMATION: syntetic polypeptide

<400> SEQUENCE: 4

Gly Gly Thr Arg Ser Pro Arg Cys Asp Cys Ala Gly Asp Phe His Lys
1               5                   10                  15

Lys Tyr Gly Leu Phe Cys Cys Arg Gly Cys Pro Ala Gly His Tyr Leu
            20                  25                  30

Lys Ala Pro Cys Thr Glu Pro Cys Gly Asn Ser Thr Cys Leu Val Cys
        35                  40                  45

Pro Gln Gly Thr Phe Leu Ala Trp Glu Asn His His Asn Ser Glu Cys
    50                  55                  60

Ala Arg Cys Gln Ala Cys Asp Glu Gln Ala Ser Gln Val Ala Leu Glu
65                  70                  75                  80

Asn Cys Ser Ala Val Ala Asp Thr Arg Cys Gly Cys Glu Pro Gly Trp
                85                  90                  95
```

Phe Val Glu Cys Gln Val Ser Gln Cys Val Ser Ser Ser Pro Phe Tyr
100 105 110

Cys Gln Pro Cys Leu Asp Cys Gly Ala Leu His Arg His Thr Arg Leu
115 120 125

Pro Cys Ser Arg Arg Asp Thr Asp Cys Gly Thr Cys Leu Pro Gly Phe
130 135 140

Tyr Glu His Gly Asp Gly Cys Val Ser Cys Pro Thr Ser Thr Leu Gly
145 150 155 160

Ser Cys Pro Glu Arg Cys Ala Ala Val Cys Gly Trp Arg Gln Met Phe
165 170 175

<210> SEQ ID NO 5
<211> LENGTH: 176
<212> TYPE: PRT
<213> ORGANISM: Artificial sequence
<220> FEATURE:
<223> OTHER INFORMATION: syntetic polypeptide

<400> SEQUENCE: 5

Gly Gly Thr Arg Ser Pro Arg Cys Asp Cys Ala Gly Asp Phe His Lys
1 5 10 15

Lys Ile Gly Leu Phe Cys Cys Arg Gly Cys Pro Ala Gly His Tyr Leu
20 25 30

Lys Ala Pro Cys Thr Lys Pro Cys Gly Asn Ser Thr Cys Leu Pro Cys
35 40 45

Pro Gln Asp Thr Phe Leu Ala Arg Glu Asn His His Asn Ser Glu Cys
50 55 60

Thr Arg Cys Gln Ala Cys Asp Glu Gln Ala Ser Gln Val Ala Leu Glu
65 70 75 80

Asn Cys Ser Ala Val Ala Asp Thr Arg Cys Gly Cys Ala Pro Gly Trp
85 90 95

Phe Val Glu Cys Ser Val Ser Gln Cys Val Ser Ser Ser Pro Phe Tyr
100 105 110

Cys Gln Pro Cys Leu Asp Cys Gly Ala Leu His Arg His Thr Arg Leu
115 120 125

Pro Cys Ser Arg Arg Asp Thr Asp Cys Gly Thr Cys Leu Pro Gly Phe
130 135 140

Tyr Glu His Gly Asp Gly Cys Val Ser Cys Pro Thr Ser Thr Leu Gly
145 150 155 160

Ser Cys Pro Glu Arg Cys Ala Ala Val Cys Gly Trp Arg Gln Met Phe
165 170 175

<210> SEQ ID NO 6
<211> LENGTH: 176
<212> TYPE: PRT
<213> ORGANISM: Artificial sequence
<220> FEATURE:
<223> OTHER INFORMATION: syntetic polypeptide

<400> SEQUENCE: 6

Gly Gly Thr Arg Ser Pro Arg Cys Asp Cys Ala Gly Asp Phe Gln Lys
1 5 10 15

Lys Ile Gly Leu Phe Cys Cys Arg Gly Cys Pro Ala Gly His Tyr Leu
20 25 30

Lys Ala Pro Cys Thr Glu Pro Cys Gly Asn Ser Thr Cys Leu Pro Cys
35 40 45

Pro Gln Asp Thr Phe Leu Ala Arg Glu Asn His His Asn Ser Glu Cys

-continued 50 55 60

Ala Arg Cys Gln Ala Cys Asp Glu Gln Ala Ser Gln Val Ala Leu Glu
65 70 75 80

Asn Cys Ser Ala Val Ala Asp Thr Arg Cys Gly Cys Lys Pro Gly Trp
85 90 95

Phe Val Glu Cys Gln Val Ser Pro Cys Val Ser Ser Ser Pro Phe Tyr
100 105 110

Cys Gln Pro Cys Leu Asp Cys Gly Ala Leu His Arg His Thr Arg Leu
115 120 125

Leu Cys Ser Arg Arg Asp Thr Asp Cys Gly Thr Cys Leu Pro Gly Phe
130 135 140

Tyr Glu His Gly Asp Gly Cys Val Ser Cys Pro Thr Ser Thr Leu Gly
145 150 155 160

Ser Cys Pro Glu Arg Cys Ala Ala Val Cys Gly Trp Arg Gln Met Phe
165 170 175

<210> SEQ ID NO 7
<211> LENGTH: 176
<212> TYPE: PRT
<213> ORGANISM: Artificial sequence
<220> FEATURE:
<223> OTHER INFORMATION: syntetic polypeptide

<400> SEQUENCE: 7

Gly Gly Thr Arg Ser Pro Arg Cys Asp Cys Ala Gly Asp Phe His Lys
1 5 10 15

Lys Ile Gly Leu Phe Cys Cys Arg Gly Cys Pro Ala Gly His Tyr Leu
20 25 30

Lys Ala Pro Cys Thr Lys Pro Cys Gly Asn Ser Thr Cys Leu Pro Cys
35 40 45

Pro Gln Asp Thr Phe Leu Ala Trp Glu Asn His His Asn Ser Glu Cys
50 55 60

Thr Arg Cys Gln Ala Cys Asp Glu Gln Ala Ser Gln Val Ala Leu Glu
65 70 75 80

Asn Cys Ser Ala Val Ala Asp Thr Arg Cys Gly Cys Lys Pro Gly Trp
85 90 95

Phe Val Glu Cys Ser Val Ser Gln Cys Val Ser Ser Ser Pro Phe Tyr
100 105 110

Cys Gln Pro Cys Leu Asp Cys Gly Ala Leu His Arg His Thr Arg Leu
115 120 125

Leu Cys Ser Arg Arg Asp Thr Asp Cys Gly Thr Cys Leu Pro Gly Phe
130 135 140

Tyr Glu His Gly Asp Gly Cys Val Ser Cys Pro Thr Ser Thr Leu Gly
145 150 155 160

Ser Cys Pro Glu Arg Cys Ala Ala Val Cys Gly Trp Arg Gln Met Phe
165 170 175

<210> SEQ ID NO 8
<211> LENGTH: 176
<212> TYPE: PRT
<213> ORGANISM: Artificial sequence
<220> FEATURE:
<223> OTHER INFORMATION: syntetic polypeptide

<400> SEQUENCE: 8

Gly Gly Thr Arg Ser Pro Arg Cys Asp Cys Ala Gly Asp Phe Gln Lys
1 5 10 15

-continued

```
Lys Ile Gly Leu Phe Cys Cys Arg Gly Cys Pro Ala Gly His Tyr Leu
            20                  25                  30

Lys Ala Pro Cys Thr Lys Pro Cys Gly Asn Ser Thr Cys Leu Pro Cys
        35                  40                  45

Pro Gln Gly Thr Phe Leu Ala Trp Glu Asn His His Glu Ser Glu Cys
    50                  55                  60

Ala Arg Cys Gln Ala Cys Asp Glu Gln Ala Ser Gln Val Ala Leu Glu
65                  70                  75                  80

Asn Cys Ser Ala Val Ala Asp Thr Arg Cys Gly Cys Ala Pro Gly Trp
                85                  90                  95

Phe Val Glu Cys Ser Val Ser Gln Cys Val Ser Ser Ser Pro Phe Tyr
            100                 105                 110

Cys Gln Pro Cys Leu Asp Cys Gly Ala Leu His Arg His Thr Arg Leu
        115                 120                 125

Leu Cys Ser Arg Arg Asp Thr Asp Cys Gly Thr Cys Leu Pro Gly Phe
    130                 135                 140

Tyr Glu His Gly Asp Gly Cys Val Ser Cys Pro Thr Ser Thr Leu Gly
145                 150                 155                 160

Ser Cys Pro Glu Arg Cys Ala Ala Val Cys Gly Trp Arg Gln Met Phe
                165                 170                 175


<210> SEQ ID NO 9
<211> LENGTH: 176
<212> TYPE: PRT
<213> ORGANISM: Artificial sequence
<220> FEATURE:
<223> OTHER INFORMATION: syntetic

<400> SEQUENCE: 9

Gly Gly Thr Arg Ser Pro Arg Cys Asp Cys Ala Gly Asp Phe Gln Lys
1               5                   10                  15

Lys Ile Gly Leu Phe Cys Cys Arg Gly Cys Pro Ala Gly His Tyr Leu
            20                  25                  30

Lys Ala Pro Cys Thr Glu Pro Cys Gly Asn Ser Thr Cys Leu Pro Cys
        35                  40                  45

Pro Gln Asp Thr Phe Leu Ala Trp Glu Asn His His Glu Ser Glu Cys
    50                  55                  60

Ala Arg Cys Gln Ala Cys Asp Glu Gln Ala Ser Gln Val Ala Leu Glu
65                  70                  75                  80

Asn Cys Ser Ala Val Ala Asp Thr Arg Cys Gly Cys Glu Pro Gly Trp
                85                  90                  95

Phe Val Glu Cys Ser Val Ser Pro Cys Val Ser Ser Ser Pro Phe Tyr
            100                 105                 110

Cys Gln Pro Cys Leu Asp Cys Gly Ala Leu His Arg His Thr Arg Leu
        115                 120                 125

Pro Cys Ser Arg Arg Asp Thr Asp Cys Gly Thr Cys Leu Pro Gly Phe
    130                 135                 140

Tyr Glu His Gly Asp Gly Cys Val Ser Cys Pro Thr Ser Thr Leu Gly
145                 150                 155                 160

Ser Cys Pro Glu Arg Cys Ala Ala Val Cys Gly Trp Arg Gln Met Phe
                165                 170                 175


<210> SEQ ID NO 10
<211> LENGTH: 223
<212> TYPE: PRT
<213> ORGANISM: Artificial sequence
<220> FEATURE:
```

<223> OTHER INFORMATION: syntetic peptide

<400> SEQUENCE: 10

Val Glu Cys Pro Pro Cys Pro Ala Pro Pro Val Ala Gly Pro Ser Val
1               5                   10                  15

Phe Leu Phe Pro Pro Lys Pro Lys Asp Thr Leu Met Ile Ser Arg Thr
            20                  25                  30

Pro Glu Val Thr Cys Val Val Val Asp Val Ser His Glu Asp Pro Glu
        35                  40                  45

Val Lys Phe Asn Trp Tyr Val Asp Gly Val Glu Val His Asn Ala Lys
    50                  55                  60

Thr Lys Pro Arg Glu Glu Gln Tyr Asn Ser Thr Tyr Arg Val Val Ser
65                  70                  75                  80

Val Leu Thr Val Leu His Gln Asp Trp Leu Asn Gly Lys Glu Tyr Lys
                85                  90                  95

Cys Lys Val Ser Asn Lys Gly Leu Pro Ser Ser Ile Glu Lys Thr Ile
            100                 105                 110

Ser Lys Ala Lys Gly Gln Pro Arg Glu Pro Gln Val Tyr Thr Leu Pro
        115                 120                 125

Pro Ser Arg Glu Glu Met Thr Lys Asn Gln Val Ser Leu Thr Cys Leu
    130                 135                 140

Val Lys Gly Phe Tyr Pro Ser Asp Ile Ala Val Glu Trp Glu Ser Asn
145                 150                 155                 160

Gly Gln Pro Glu Asn Asn Tyr Lys Thr Thr Pro Pro Val Leu Asp Ser
                165                 170                 175

Asp Gly Ser Phe Phe Leu Tyr Ser Lys Leu Thr Val Asp Lys Ser Arg
            180                 185                 190

Trp Gln Gln Gly Asn Val Phe Ser Cys Ser Val Met His Glu Gly Leu
        195                 200                 205

His Asn His Tyr Thr Gln Lys Ser Leu Ser Leu Ser Pro Gly Lys
    210                 215                 220

<210> SEQ ID NO 11
<211> LENGTH: 8
<212> TYPE: PRT
<213> ORGANISM: Artificial sequence
<220> FEATURE:
<223> OTHER INFORMATION: syntetic polypeptide

<400> SEQUENCE: 11

Ile Glu Gly Arg Met Asp Arg Ser
1               5

<210> SEQ ID NO 12
<211> LENGTH: 1224
<212> TYPE: DNA
<213> ORGANISM: Artificial sequence
<220> FEATURE:
<223> OTHER INFORMATION: syntetic

<400> SEQUENCE: 12
ggcggcactc gtagccccag gtgtgactgt gccggtgact tccacaagaa gattggtctg      60
ttttgttgca gaggctgccc agcggggcac tacctgaagg ccccttgcac ggagccctgc     120
ggcaactcca cctgccttgt gtgtccccaa gacaccttct tggcctggga gaaccaccat     180
aattctgaat gtgcccgctg ccaggcctgt gatgagcagg cctcccaggt ggcgctggag     240
aactgttcag cagtggccga cacccgctgt ggctgtaagc caggctggtt tgtggagtgc     300

-continued

```
caggtcagcc aatgtgtcag cagttcaccc ttctactgcc aaccatgcct agactgcggg    360

gccctgcacc gccacacacg gctactctgt tcccgcagag atactgactg tgggacctgc    420

ctgcctggct tctatgaaca tggcgatggc tgcgtgtcct gccccacgag caccctgggg    480

agctgtccag agcgctgtgc cgctgtctgt ggctggaggc agatgttcat cgagggacgg    540

atggacagat ctgtggagtg cccaccttgc ccagcaccac ctgtggcagg accttcagtc    600

ttcctcttcc ccccaaaacc caaggacacc ctcatgatct cccggacccc tgaggtcaca    660

tgcgtggtgg tggacgtgag ccacgaagac cctgaggtca agttcaactg gtacgtggac    720

ggcgtggagg tgcataatgc caagacaaag ccgcgggagg agcagtacaa cagcacgtac    780

cgtgtggtca gcgtcctcac cgtcctgcac caggactggc tgaatggcaa ggagtacaag    840

tgcaaggtct ccaacaaagg cctcccatcc tccatcgaga aaaccatctc caaagccaaa    900

gggcagcccc gagaaccaca ggtgtacacc ctgcccccat cccgggagga gatgaccaag    960

aaccaggtca gcctgacctg cctggtcaaa ggcttctatc ccagcgacat cgccgtggag   1020

tgggagagca atgggcagcc ggagaacaac tacaagacca cgcctcccgt gctggactcc   1080

gacggctcct tcttcctcta cagcaagctc accgtggaca agagcaggtg gcagcagggg   1140

aacgtcttct catgctccgt gatgcatgag ggtctgcaca accactacac gcagaagagc   1200

ctctccctgt ctccgggtaa atga                                          1224
```

```
<210> SEQ ID NO 13
<211> LENGTH: 176
<212> TYPE: PRT
<213> ORGANISM: Homo sapiens

<400> SEQUENCE: 13

Gly Gly Thr Arg Ser Pro Arg Cys Asp Cys Ala Gly Asp Phe His Lys
1               5                   10                  15

Lys Ile Gly Leu Phe Cys Cys Arg Gly Cys Pro Ala Gly His Tyr Leu
            20                  25                  30

Lys Ala Pro Cys Thr Glu Pro Cys Gly Asn Ser Thr Cys Leu Val Cys
        35                  40                  45

Pro Gln Asp Thr Phe Leu Ala Trp Glu Asn His His Asn Ser Glu Cys
    50                  55                  60

Ala Arg Cys Gln Ala Cys Asp Glu Gln Ala Ser Gln Val Ala Leu Glu
65                  70                  75                  80

Asn Cys Ser Ala Val Ala Asp Thr Arg Cys Gly Cys Lys Pro Gly Trp
                85                  90                  95

Phe Val Glu Cys Gln Val Ser Gln Cys Val Ser Ser Ser Pro Phe Tyr
            100                 105                 110

Cys Gln Pro Cys Leu Asp Cys Gly Ala Leu His Arg His Thr Arg Leu
        115                 120                 125

Leu Cys Ser Arg Arg Asp Thr Asp Cys Gly Thr Cys Leu Pro Gly Phe
    130                 135                 140

Tyr Glu His Gly Asp Gly Cys Val Ser Cys Pro Thr Ser Thr Leu Gly
145                 150                 155                 160

Ser Cys Pro Glu Arg Cys Ala Ala Val Cys Gly Trp Arg Gln Met Phe
                165                 170                 175


<210> SEQ ID NO 14
<211> LENGTH: 16
<212> TYPE: PRT
<213> ORGANISM: artificial sequence
<220> FEATURE:
```

<223> OTHER INFORMATION: fragment

<400> SEQUENCE: 14

Thr Cys Leu Val Cys Pro Gln Asp Thr Phe Leu Ala Trp Glu Asn His
1 5 10 15

<210> SEQ ID NO 15
<211> LENGTH: 16
<212> TYPE: PRT
<213> ORGANISM: Artificial sequence
<220> FEATURE:
<223> OTHER INFORMATION: fragment

<400> SEQUENCE: 15

Thr Cys Leu Leu Cys Pro Gln Asp Thr Phe Leu Ala Trp Glu Asn His
1 5 10 15

<210> SEQ ID NO 16
<211> LENGTH: 16
<212> TYPE: PRT
<213> ORGANISM: Artificial sequence
<220> FEATURE:
<223> OTHER INFORMATION: fragment

<400> SEQUENCE: 16

Thr Cys Leu Pro Cys Pro Gln Gly Thr Phe Leu Ala Arg Glu Asn His
1 5 10 15

<210> SEQ ID NO 17
<211> LENGTH: 16
<212> TYPE: PRT
<213> ORGANISM: Artificial sequence
<220> FEATURE:
<223> OTHER INFORMATION: fragment

<400> SEQUENCE: 17

Thr Cys Leu Pro Cys Pro Gln Gly Thr Phe Leu Ala Trp Glu Asn His
1 5 10 15

<210> SEQ ID NO 18
<211> LENGTH: 16
<212> TYPE: PRT
<213> ORGANISM: Artificial sequence
<220> FEATURE:
<223> OTHER INFORMATION: fragment

<400> SEQUENCE: 18

Thr Cys Leu Pro Cys Pro Gln Gly Thr Phe Leu Ala Arg Lys Asn His
1 5 10 15

<210> SEQ ID NO 19
<211> LENGTH: 16
<212> TYPE: PRT
<213> ORGANISM: Artificial sequence
<220> FEATURE:
<223> OTHER INFORMATION: fragment

<400> SEQUENCE: 19

Ile Cys Leu Pro Cys Pro Trp Gly Thr Phe Leu Ala Arg Glu Asn His
1 5 10 15

<210> SEQ ID NO 20
<211> LENGTH: 16
<212> TYPE: PRT
<213> ORGANISM: Artificial sequence
<220> FEATURE:
<223> OTHER INFORMATION: fragment -continued

<400> SEQUENCE: 20

Thr Cys Leu Pro Cys Pro Gln Gly Thr Phe Leu Ala Arg Glu Asn His
1 5 10 15

<210> SEQ ID NO 21
<211> LENGTH: 16
<212> TYPE: PRT
<213> ORGANISM: Artificial sequence
<220> FEATURE:
<223> OTHER INFORMATION: fragment

<400> SEQUENCE: 21

Thr Cys Leu Pro Cys Pro Ser Asp Thr Phe Leu Thr Arg Asp Asn His
1 5 10 15

<210> SEQ ID NO 22
<211> LENGTH: 16
<212> TYPE: PRT
<213> ORGANISM: Artificial sequence
<220> FEATURE:
<223> OTHER INFORMATION: fragment

<400> SEQUENCE: 22

Thr Cys Leu Pro Cys Pro Arg Gly Thr Phe Leu Thr Trp Gly Asn His
1 5 10 15

<210> SEQ ID NO 23
<211> LENGTH: 16
<212> TYPE: PRT
<213> ORGANISM: Artificial sequence
<220> FEATURE:
<223> OTHER INFORMATION: fragment

<400> SEQUENCE: 23

Ser Cys Leu Pro Cys Pro Pro Gly Thr Phe Leu Ala Arg Asp Ser His
1 5 10 15

<210> SEQ ID NO 24
<211> LENGTH: 16
<212> TYPE: PRT
<213> ORGANISM: Artificial sequence
<220> FEATURE:
<223> OTHER INFORMATION: fragment

<400> SEQUENCE: 24

Thr Cys Leu Pro Cys Pro Gln Gly Thr Phe Leu Ala Arg Glu Asn His
1 5 10 15

<210> SEQ ID NO 25
<211> LENGTH: 16
<212> TYPE: PRT
<213> ORGANISM: Artificial sequence
<220> FEATURE:
<223> OTHER INFORMATION: fragment

<400> SEQUENCE: 25

Thr Cys Leu Pro Cys Pro Arg Gly Thr Phe Leu Ala Arg Glu Asn His
1 5 10 15